(12) United States Patent
Holzmann et al.

(10) Patent No.: US 10,711,276 B2
(45) Date of Patent: Jul. 14, 2020

(54) SEQUENCE VARIANTS

(71) Applicant: Sandoz AG, Basel (CH)

(72) Inventors: Johann Holzmann, Kundl (AT); Michael Fuchs, Kundl (AT); Clemens Achmüller, Kundl (AT); Hansjörg Toll, Kundl (AT)

(73) Assignee: Sandoz AG, Basel (CH)

( * ) Notice: Subject to any disclaimer, the term of this patent is extended or adjusted under 35 U.S.C. 154(b) by 168 days.

(21) Appl. No.: 15/537,925

(22) PCT Filed: Dec. 18, 2015

(86) PCT No.: PCT/EP2015/080512
§ 371 (c)(1),
(2) Date: Jun. 20, 2017

(87) PCT Pub. No.: WO2016/102372
PCT Pub. Date: Jun. 30, 2016

(65) Prior Publication Data
US 2017/0342422 A1    Nov. 30, 2017

(30) Foreign Application Priority Data

Dec. 22, 2014 (EP) ..................... 14199893

(51) Int. Cl.
| | | |
|---|---|---|
| *C12Q 1/68* | (2018.01) | |
| *C12N 15/67* | (2006.01) | |
| *C12N 15/70* | (2006.01) | |
| *C12Q 1/6858* | (2018.01) | |
| *C12Q 1/6869* | (2018.01) | |
| *C12N 15/10* | (2006.01) | |
| *C12N 15/85* | (2006.01) | |

(52) U.S. Cl.
CPC ............ *C12N 15/67* (2013.01); *C12N 15/70* (2013.01); *C12Q 1/6858* (2013.01); *C12Q 1/6869* (2013.01); *C12N 15/1072* (2013.01); *C12N 2015/8518* (2013.01)

(58) Field of Classification Search
CPC ...... C12N 15/67; C12N 15/70; C12Q 1/6858; C12Q 1/6869
See application file for complete search history.

(56) References Cited

U.S. PATENT DOCUMENTS

2018/0051065 A1* 2/2018 Yin .......................... C07K 1/02

OTHER PUBLICATIONS

Search Report and Written Opinion for PCT/EP2015/080512, 10 pages.
Qian, Wenfeng, et al., Balanced Codon Usage Optimized Eukaryotic Translational Efficiency, PLOS Genetics, Mar. 29, 2012.
Chung, Bevan Kai-Sheng, et al., Computational codon optimization of synthetic gene for protein expression, BMC Systems Biology, 2012.
Chithambaram, Shivapriya, et al., Differential codon adaptation between dsDNA and ssDNA phages in *Escherichia coli*, Mol. Biol. Evol. vol. 31, issue 6, Feb. 27, 2014, pp. 1606-1617.
The Finely Tuned Genetic Code, Evolution News, Nov. 19, 2011, https://evolutionnews.org/2011/11/the_finely_tuned_genetic_code/.
Chung Bevan Kai-Sheng et al., Computational codon optimization of synthetic gene for protein expression, BMC Systems Biology, vol. 6, Oct. 2012.
Chithambaram Shivapriya et al., Differential codon adaptation between dsDNA and ssDNA phages in *Escherichia coli*, vol. 31, No. 6, Jun. 2014, pp. 1606-1617.
Plotkin Joshua B et al., Synonymous but not the same: the causes and consequences of codon bias, Nature Reviews Genetics, Nature Publishing Group, vol. 12, No. 1, Jan. 1, 2011, pp. 32-42.
Qian Wenfeng et al., Balanced codon usage optimizes eukaryotic translational efficiency, Plos Genetics, vol. 8, No. 3, Mar. 2012.
Yu, X. Christopher, et al., Identification of Codon-Specific Serine to Asparagine Mistranslation in Recombinant Monoclonal Antibodies by High-Resolution Mass Spectrometry, Anal. Chem. 2009, vol. 81, pp. 9282-9290.
Nechansky, Andreas, et al., Immunogenicity of therapeutics: a matter of efficacy and safety, Expert Opinion, Drug Discovery 2010, 5(11):1067-1079.
Harding, Fiona A., et al., The immunogenicity of humanized and fully human antibodies, MAbs 2010, 2(3), pp. 256-265.
Weber, Constanze A., et al., T cell epitope: Friend or Foe? Immunogenicity of biologics in context, Advanced Drug Delivery Reviews, 2009, vol. 61, pp. 965-976.
Roque-Navarro, Lourdes, et al., Humanization of Predicted T-Cell Epitopes Reduces the Immunogenicity of Chimeric Antibodies: New Evidence Supporting a Simple Method, Hybridoma and Hybridomics, 2003, vol. 22, No. 4, pp. 245-257.
Tangri, S., et al., Rationally Engineered Proteins or Antibodies with Absent or Reduced Immunogenicity, Current Medicinal Chemistry, 2002, vol. 9, pp. 2191-2199.

(Continued)

*Primary Examiner* — Antonio Galisteo Gonzalez
(74) *Attorney, Agent, or Firm* — Luedeka Neely Group, P.C.

(57) ABSTRACT

Amino acid residue misincorporations are necessarily found in sequence variants at low concentrations in admixture with expressed polypeptides, resulting from one or more base mismatches within codons susceptible to amino acid residue misincorporation during transcription and/or translation. The invention provides a method of optimizing the coding sequences of a polynucleotide that encodes a polypeptide, wherein at least one codon is susceptible to amino acid residue misincorporation. The method of the invention can be used to reverse-engineer an unknown coding sequence, which encodes the same polypeptide, but differs in said at least one codon from the known coding sequence. The method can further be used to alter the immunogenic potential of an expressed polypeptide. Thus, the invention is useful in engineering optimized polynucleotides encoding polypeptides.

13 Claims, 6 Drawing Sheets

Specification includes a Sequence Listing.

(56) References Cited

OTHER PUBLICATIONS

Mateo, Cristina, et al., Removal of Amphipathic Epitopes from Genetically Engineered Antibodies: Production of Modified Immunoglobulins with Reduced Immunogenicity, Hybridoma, 2000, vol. 19, No. 6, pp. 463-471.
De Groot, Anne S., et al., Immunoinformatic comparison of T-cell epitopes contained in novel awine-origin influenza A (H1N1) virus with epitopes in 2008-2009 conventional influenza vaccine, Vaccine, 2009, vol. 27, pp. 5740-5747.
Chervet, J.P., et al., Instrumental Requirements for Nanoscale Liquid Chromatography, Analytical Chemistry 1996, vol. 68, pp. 1507-1512.
Parker, J., et al., Stuttering: High-level mistranslation in animal and bacterial cells, Proc. Natl. Acad. Sci. USA, 1978, vol. 7, No. 3, 1091-5.
Kunkel, Bebenek, et al., DNA Replication Fidelity, Annual Rev. Biochem. 2000; vol. 69, pp. 497-529.
Loftfield, Robert, et al., The Frequency of Errors in Protein Biosynthesis, Biochem. J. 1972, vol. 128, pp. 1353-1356.
Melmer, Michael, et al., HILIC analysis of fluorescence-labeled N-glycans from recombinant biopharmaceuticals, Anal. Bioanal. Chem., 2010, vol. 398, pp. 905-914.
Melmer, Michael, et al, Comparison of hydrophilic-interaction, reversed-phased and porous graphitic carbon chromatography for glycan analysis, Journal of Chromatography A, 2011, vol. 1218, pp. 118-123.
Sydow, Jasmin F., et al., RNA Polymerase fidelity and transcriptional proofreading, Current Opinion in Structural Biology, 2009, vol. 19, pp. 732-739.
Schluter, Hartmut, Protein Liquid Chromatography, Journal of Chromatography Library, 2000, vol. 61, p. 153.

\* cited by examiner

FIG. 6

SEQUENCE LISTING

```
<160> NUMBER OF SEQ ID NOS: 7

<210> SEQ ID NO 1
<211> LENGTH: 14
<212> TYPE: PRT
<213> ORGANISM: Artificial Sequence
<220> FEATURE:
<223> OTHER INFORMATION: Peptide fragment

<400> SEQUENCE: 1
```

Ser Thr Ser Gly Gly Thr Ala Ala Leu Gly Cys Leu Val Lys
1               5                   10

<210> SEQ ID NO 2
<211> LENGTH: 14
<212> TYPE: PRT
<213> ORGANISM: Artificial Sequence
<220> FEATURE:
<223> OTHER INFORMATION: Peptide fragment

<400> SEQUENCE: 2

Ser Thr Ser Glu Gly Thr Ala Ala Leu Gly Cys Leu Val Lys
1               5                   10

<210> SEQ ID NO 3
<211> LENGTH: 14
<212> TYPE: PRT
<213> ORGANISM: Artificial Sequence
<220> FEATURE:
<223> OTHER INFORMATION: Peptide fragment

<400> SEQUENCE: 3

Ser Thr Ser Gly Asp Thr Ala Ala Leu Gly Cys Leu Val Lys
1               5                   10

<210> SEQ ID NO 4
<211> LENGTH: 14
<212> TYPE: PRT
<213> ORGANISM: Artificial Sequence
<220> FEATURE:
<223> OTHER INFORMATION: Peptide fragment

<400> SEQUENCE: 4

Ser Thr Ser Gly Gly Thr Ala Ala Leu Asp Cys Leu Val Lys
1               5                   10

<210> SEQ ID NO 5
<211> LENGTH: 16
<212> TYPE: PRT
<213> ORGANISM: Artificial Sequence
<220> FEATURE:
<223> OTHER INFORMATION: Peptide fragment

<400> SEQUENCE: 5

Val Val Ser Val Leu Thr Val Leu His Gln Asp Trp Leu Asn Gly Lys
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: Peptide fragment

<400> SEQUENCE: 6

Gly Arg Gly Leu Glu Trp Ile Gly Ala Ile Tyr Pro Gly Asn Gly
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: Peptide Fragment

```
<400> SEQUENCE: 7

Gly Asp Trp Tyr Phe Asn Val Trp Gly Ala Gly Thr Thr Val Thr
1               5                   10                  15
```

SEQUENCE VARIANTS

This application is a Section 371 national phase entry of PCT application PCT/EP2015/080512, filed Dec. 18, 2015. This application also claims the benefit of the earlier filing date of European patent application 1419989.3, filed Dec. 22, 2014.

This application contains a Sequence Listing which has been submitted electronically in ASCII format and is herein incorporated by reference. The ASCII file, created on Jan. 13, 2016, is named 72824us-SequenceListing.txt, and is 1731 bytes in size.

FIELD OF THE INVENTION

The invention relates to a method of optimizing the coding sequences of a polynucleotide that encodes a polypeptide, wherein at least one codon is susceptible to amino acid residue misincorporation. This method can be used to reverse-engineer at least one codon of a second, unknown coding sequence, which encodes the same polypeptide, but differs in said at least one codon from the known coding sequence. The method of the invention can further be used to alter the immunogenic potential of an expressed polypeptide. At last, the invention also encompasses a method for engineering an optimized polynucleotide that encodes a polypeptide.

BACKGROUND

Protein therapeutics are increasingly common in treating various conditions. For these products to be safe, reproducible and effective in a patient, high fidelity transcription and translation of a given polynucleotide sequence into the "correct" amino acid polypeptide product, yielding a product of high homogeneity, is critical to pharmaceutical production of human proteins in any expression system or host cell including *Escherichia coli*, yeast, or mammalian cells, for instance, Chinese hamster ovary (CHO) cells.

Low abundance protein sequence variants, having an amino acid primary sequence which differs from that encoded by the respective coding region of a polynucleotide used for expression, are found in essentially every expressed protein and can be accounted for product-dependent impurities in a protein therapeutic. These low abundance sequence variants are the result of amino acid residue misincorporations due to nucleotide mismatches during transcription and/or translation. Whether or not a nucleotide mismatch at the transcriptional and/or the translational level leads to an exchange of differing amino acid residues by misincorporation, e.g., Gly→Glu, or Gly→Asp, is primarily dependent from the type of codon encoding said amino acid residue at the level of the encoding polynucleotide sequence.

Any heterogeneity or deviation from the "correct" or native encoded amino acid sequence of a polypeptide product can lead to significant disadvantages including lower quality, increased purification effort, altered therapeutic efficacy and/or altered immunogenicity, e.g., increased immunogenicity. Two protein products obtainable by expression in any expression system may substantially differ in the afore-mentioned characteristics even where their respective coding sequences are highly similar or almost identical, but differ in at least one codon encoding the same amino acid in the same respective position of the protein. Thus, protein products which are not obtained by expression of exactly the identical coding sequence, can show different immunological properties, for example, induction of antibody formation directed against said proteins, and/or different pharmacological properties, for example, a differing half-life or differing pharmacokinetics.

For these reasons, it is desirable to have a method available which could be used to either provide a coding sequence which is more or less prone to amino acid misincorporation, or to provide the unknown coding sequence of a known, previously characterized and/or marketed protein product, in order to exactly match the degree or type of amino acid residue misincorporation of said known product. The latter aspect of such method is particularly relevant in the development of biosimilar pharmaceutics, where the product's protein sequence is fully known, or can be readily determined experimentally by routine methods, but the encoding polynucleotide sequence or a part thereof is proprietary, non-disclosed or otherwise unknown. The degree or type of impurities by low level sequence variants can be highly significant in an original protein therapeutic and/or a corresponding biosimilar therapeutic.

Yu et al., Anal. Chem. 2009, 81, 9282-9290 describes mass spectrometry-based analytics and molecular mechanisms resulting in the formation of low level sequence variants of polypeptides, comprising misincorporated amino acids. Yu et al. explains that the majority of low level sequence variants of polypeptides comprising at least one misincorporated amino acid results from at least one non-Watson-Crick base mismatch during transcription or translation. Yu et al., however, does not teach to optimize the coding sequence of a polynucleotide encoding the polypeptide, e.g., by identification and selection of at least one codon of an unknown second polynucleotide, coding for the same polypeptide but differing in at least said one codon. In other words, Yu et al. does not envisage reverse engineering of at least one codon of an unknown coding sequence.

More generally, a deduction of a coding RNA or DNA sequence from the encoded protein sequence was so far not deemed possible, due to the central dogma of molecular biology concerning the flow of genetic information within any living organism and due to the degeneracy of the genetic code.

Thus, there is a need in the biopharmaceutical industry for methods for optimizing a coding sequence encoding a polypeptide by reverse-engineering of at least one codon of an unknown coding polynucleotide sequence or parts thereof which encodes a known protein product.

Further, immunogenic activity of biopharmaceuticals, and protein therapeutics in particular, is a problem commonly encountered in the biotech industry. Specifically, the presence of T-cell epitopes in a biopharmaceutical and the occurrence of anti-drug antibodies (ADA) has now been described for a number of protein drugs demonstrating that the T cell epitope content is a significant factor that contributes to antigenicity (Shankar et al. Nat Biotechnol 2007, 25(5):555-61; Nechansky & Kircheis Expert Opin. Drug Discov 2010, 5(11):1067-1079; Harding et al. MAbs 2010, 2(3):256-65). One key determinant of T-cell activation (T-helper cells; CD4+ cells) is the binding strength of T cell epitopes to major histocompatibility complex (Type II of MHC or HLA) molecules (Weber et al. Adv Drug Deliv Rev. 2009, 30; 61(11):965-76). Considerable effort has been undertaken to estimate and reduce the immunogenic potential of protein therapeutics by predicting potential T-cell epitopes using in silico tools (Roque-Navarro et al. Hybrid Hybridomics 2003, 22(4):245-57; Tangri et al. Current Medicinal Chemistry 2002, 9:2191-9; Mateo et al. Hybridoma 2000, 19(6):463-71; De Groot et al. Vaccine 2009, 27:5740-7). Based on the predicted MHC II binding strength of a peptide sequence it is possible to make an informed decision about the likelihood that the peptide sequence will provoke an immune response. Nevertheless, prediction, alteration, or reduction of the immunogenic potential of polypeptide pharmaceuticals, has so far been limited to the "main" or native polypeptide obtainable by expression and/or purification procedures, i.e. to the amino acid sequence encoded by the respective coding sequence of a polynucleotide according to the genetic code used by the organism or host organism expressing such polypeptide.

The above cited prior art, however, did not appreciate or address the problem that the primary amino acid sequence can vary in a considerable portion of the total amount of a polypeptide drug due to mistranscriptional and/or mistranslational events resulting in one or more amino acid residue misincorporation(s) within low level sequence variants of the main or native polypeptide. It has also not been recognized in the art that such amino acid residue misincorporation(s) may significantly affect the immunogenic potential of the respective polypeptide pharmaceuticals. Concurrently, codon selection based on the immunogenic potential of the misincorporated amino acid (and the resulting peptide sequence) has so far not been performed or suggested. More specifically, the immunogenic potential of amino acid misincorporations within protein drugs has also not been included in the attempts in the prior art to alter, i.e., decrease or increase, the immunogenic potential of a polypeptide, e.g., reducing the formation of ADA.

To conclude, there is a general need for improved methods for providing codon-optimized nucleotide sequences, which encode polypeptides having an altered, in particular a decreased immunogenic potential. In particular, there is a need for methods which are useful in obtaining optimized coding sequences encoding polypeptide drugs eliciting a decreased ADA response as compared to polypeptides expressed from the non-optimized polynucleotide when introduced into a subject.

SUMMARY OF THE INVENTION

The present invention provides a method for optimizing the coding sequence of a polynucleotide that encodes a polypeptide, the method comprising (a) identification of at least one codon within said coding sequence which is susceptible to amino acid residue misincorporation at a position within the encoded polypeptide that corresponds to said codon; (b) identification of at least one codon within said coding sequence which is susceptible to amino acid residue misincorporation at a position within the encoded polypeptide that corresponds to said codon and selecting an alternative codon to the at least one codon so as to change the degree or type of amino acid residue misincorporation; (c) changing at least one codon within said coding sequence to an alternative codon, wherein said at least one codon is susceptible to amino acid residue misincorporation at a position within the encoded polypeptide that corresponds to said codon, so as to change the degree or type of amino acid residue misincorporation; or (d) identification of at least one codon within said coding sequence which is susceptible to amino acid residue misincorporation at a position within the encoded polypeptide that corresponds to said codon and changing said codon to an alternative codon so as to change the degree or type of amino acid residue misincorporation. In one embodiment, said at least one codon is susceptible to amino acid residue misincorporation upon expression of the polynucleotide in a cell. In one embodiment, the cell is a bacterial cell or a eukaryotic cell. In a preferred embodiment, the bacterial cell is an *E. coli* cell. In another preferred embodiment, the eukaryotic cell is a mammalian cell, such as a CHO cell.

In one aspect, the method of the invention comprises determining the degree or type of amino acid residue misincorporation found in (a) the polypeptide obtained by expression of said polynucleotide to be optimized; and/or (b) a polypeptide obtainable by expression of a second polynucleotide which encodes the same polypeptide but differs in said at least one codon from the polynucleotide to be optimized.

In one embodiment, said alternative codon is selected, or said at least one codon is changed, respectively, so as to match the degree or type of amino acid residue misincorporation found within a polypeptide obtainable by expression of a second polynucleotide which encodes the same polypeptide but differs in said at least one codon from the polynucleotide to be optimized.

In a preferred embodiment, said method comprises determining the degree or type of amino acid residue misincorporation found in a polypeptide obtainable by expression of a second polynucleotide which encodes the same polypeptide but differs in said at least one codon from the polynucleotide to be optimized, wherein said alternative codon is selected, or said at least one codon is changed, respectively, so as to match the degree or type of amino acid residue misincorporation found within said polypeptide obtainable by expression of a second polynucleotide which encodes the same polypeptide but differs in said at least one codon from the polynucleotide to be optimized.

The step of determining the degree or type of at least one amino acid residue misincorporation can generally comprise any detection method suitable for detecting at least one misincorporated amino acid residue within a polypeptide comprised in a mixture of polypeptides. In a particular embodiment, the step of determining the degree or type of amino acid residue misincorporation comprises mass spectrometry. Any method of mass spectrometry known in the prior art suitable for the detection of amino acid residue misincorporations may be used. Particularly preferable in this regard is the sequencing of the peptide containing the misincorporation by tandem mass spectrometry and the subsequent quantification making use of Extracted Ion Chromatograms (EIC).

In another aspect, the amino acid residue misincorporation results in an alteration, decrease or increase in immunogenic potential of said polypeptide. Accordingly, in some embodiments, the step of selection of said alternative codon, or the change of said at least one codon, respectively, results in an alteration, i.e. an increase or decrease in immunogenic potential. Preferably, the step of selection of said alternative codon, or the change of said at least one codon, respectively, results in a decrease in immunogenic potential of said polypeptide. In one embodiment, the immunogenic potential is determined in silico, in vitro or in vivo. In a preferred embodiment, the immunogenic potential refers to the presence of T-cell epitopes within a polypeptide, as determined by methods in the prior art, e.g., in Shankar et al., 2007; Nechansky & Kircheis, 2010; Harding et al., 2010, as cited above, which are incorporated herein by reference in their entirety. In another preferred embodiment, the immunogenic potential refers to T-cell activation (e.g. T-helper cells; CD4+ cells) and/or the occurrence of anti-drug antibodies (ADA) in a subject upon administration of the polypeptide.

In an embodiment of all aspects of the invention, the amino acid residue misincorporation is present in less than 10%, less than 5%, less than 1%, less than 0.5%, less than 0.1%, or less than 0.02% of the total molar amount of the expressed polypeptide. Preferably, the amino acid residue misincorporation is present in less than 0.5%, and more preferably in less than 0.1% of the total molar amount of the expressed polypeptide.

In another embodiment of all aspects of the invention, the amino acid residue misincorporation is the result of at least one non-Watson-Crick base mismatch during transcription or translation. The at least one non-Watson-Crick base mismatch is preferably selected from the group consisting of (a) a cytosine-adenine (C*A) mismatch between a DNA template strand and an mRNA being transcribed from said DNA template strand; (b) a guanine-uracil (G*U) mismatch between the mRNA codon and an anticodon of an amino-acyl tRNA during translation; (c) a adenine-cytosine (A*C) mismatch between a DNA template strand and an mRNA being transcribed from said DNA template strand; (d) an uracil-guanine (U*G) mismatch between the mRNA codon and an anticodon of an amino-acyl tRNA during translation; (e) an adenine-adenine (A*A) mismatch between a DNA template strand and an mRNA being transcribed from said DNA template strand; or (f) an uracil-uracil (U*U) mismatch between the mRNA codon and an anticodon of an amino-acyl tRNA during translation.

The at least one non-Watson-Crick base mismatch during translation or transcription results in a base difference within said at least one codon according to the genetic code. Thus, in some embodiments of all aspects of the invention, the base difference is selected from the group consisting of A→C, A→G, C→A, C→U, G→A, G→C, G→U, U→A, U→C, and U→G, or their corresponding base differences at the DNA level. In a preferred embodiment, the base difference is selected from the group consisting of G→A, U→C, and U→A, or their corresponding base differences at the DNA level. In some embodiments, the base difference is found at the first, the second or the third position of the at least one codon. In particularly preferred embodiments, the base difference with regard to the position within the at least one codon is selected from the group consisting of G1→A, G2→A, U1→A, U1→C, U2→A, U2→C, or their corresponding base differences at the DNA level.

In another preferred embodiment of all aspects of the invention, the at least one codon being susceptible to amino acid residue misincorporation is selected from the group consisting of AGA, AGC, AGG, AGU, AUA, AUC, AUG, CGA, CGC, CGG, CGU, CUA, CUC, CUG, CUU, GCA, GCC, GCG, GCU, GGA, GGC, GGG, GGU, GUA, GUC, GUG, GUU, UAC, UAU, UCA, UCC, UCG, UCU, UGC, UGG, UGU, UUA, UUC, UUG, and UUU at the RNA level, or their corresponding codons at the DNA level. In a more preferred embodiment of the invention, the at least one codon being susceptible to amino acid residue misincorporation is selected from the group consisting of AGA, AGC, AGG, AGU, AUA, AUC, CGA, CGC, CGG, CGU, CUA, CUC, CUG, CUU, GCA, GCC, GCG, GCU, GGA, GGC, GGG, GGU, GUA, GUC, GUG, GUU, UAC, UAU, UCA, UCC, UCG, UCU, UGC, UGU, UUA, UUC, UUG, and UUU at the RNA level, or their corresponding codons at the DNA level.

In another embodiment of all aspects of the invention, the at least one codon encodes an amino acid residue selected from the group consisting of Gly, Ala, Ser, Arg, Val, Ile, Leu, Met, Phe, Tyr, Cys, Trp. In a preferred embodiment, the at least one codon encodes an amino acid residue selected from the group consisting of Gly, Ser, Arg, Val, Ile, Leu and Met. In a more preferred embodiment, the at least one codon encodes an amino acid residue selected from the group consisting of Gly, Ser, Arg, Val, Ile and Leu.

In one embodiment of all aspects of the invention, the at least one codon is GGC or GGU and aspartate is misincorporated in place of glycine. In another embodiment of all aspects of the invention, the at least one codon is GGG or GGA and glutamate is misincorporated in place of glycine. In another embodiment of all aspects of the invention, the at least one codon is GGG or GGA and arginine is misincorporated in place of glycine. In another embodiment of all aspects of the invention, the at least one codon is GGC or GGU and serine is misincorporated in place of glycine. In another embodiment of all aspects of the invention, the at least one codon is AGC or AGU and asparagine is misincorporated in place of serine. In another embodiment of all aspects of the invention, the at least one codon is CGG or CGA and glutamine is misincorporated in place of arginine. In another embodiment of all aspects of the invention, the at least one codon is CGU or CGC and histidine is misincorporated in place of arginine. In another embodiment of all aspects of the invention, the at least one codon is AGG or AGA and lysine is misincorporated in place of arginine. In another embodiment of all aspects of the invention, the at least one codon is GUA, GUU, or GUC and isoleucine is misincorporated in place of valine. In another embodiment of all aspects of the invention, the at least one codon is GUG and methionine is misincorporated in place of valine. In another embodiment of all aspects of the invention, the at least one codon is UUA or UUG and serine is misincorporated in place of leucine. In another embodiment of all aspects of the invention, the at least one codon is UCU, UCC, UCA or UCG and proline is misincorporated in place of serine. In another embodiment of all aspects of the invention, the at least one codon is GUG or GUA and glutamate is misincorporated in place of valine. In another embodiment of all aspects of the invention, the at least one codon is GUC or GUU and aspartate is misincorporated in place of valine. In another embodiment of all aspects of the invention, the at least one codon is AUA and lysine is misincorporated in place of isoleucine. In another embodiment of all aspects of the invention, the at least one codon is AUC or AUA and asparagine is misincorporated in place of isoleucine. In another embodiment of all aspects of the invention, the at least one codon is AUG and lysine is misincorporated in place of methionine. In another embodiment of all aspects of the invention, the at least one codon is CUU or CUC and histidine is misincorporated in place of leucine. In another embodiment of all aspects of the invention, the at least one codon is CUA or CUG and glutamine is misincorporated in place of leucine. In another embodiment of all aspects of the invention, the at least one codon is UUA and isoleucine is misincorporated in place of leucine. In another embodiment of all aspects of the invention, or the at least one codon is UUG and methionine is misincorporated in place of leucine.

In some embodiment of all aspects of the invention, determining the degree or type of amino acid residue misincorporation comprises the use of mass spectrometry (MS). In specific embodiments, MS comprises LC-MS/MS, HPLC-MS/MS, nano-LC-MS/MS, or nanoHPCL-MS/MS.

In one embodiment of all aspects of the invention, the polypeptide is a pharmaceutically active polypeptide. In a specific embodiment, said pharmaceutically active polypeptide is an antibody or antigen-binding fragment or fusion protein thereof.

The invention further provides a method for engineering a polynucleotide that encodes a polypeptide, comprising the following steps: (a) optimizing the coding sequence according to any one of the methods of optimizing the coding sequence of a polynucleotide that encodes a polypeptide as described and/or claimed herein; (b) substituting one or more nucleotide(s) of the polynucleotide by the corresponding nucleotide(s) of the optimized coding sequence.

BRIEF DESCRIPTION OF THE DRAWINGS

FIG. 6. Schematic depiction of codon optimization to reduce the immunogenic potential of a polypeptide.

DETAILED DESCRIPTION OF THE INVENTION

Definitions

Figure 1:
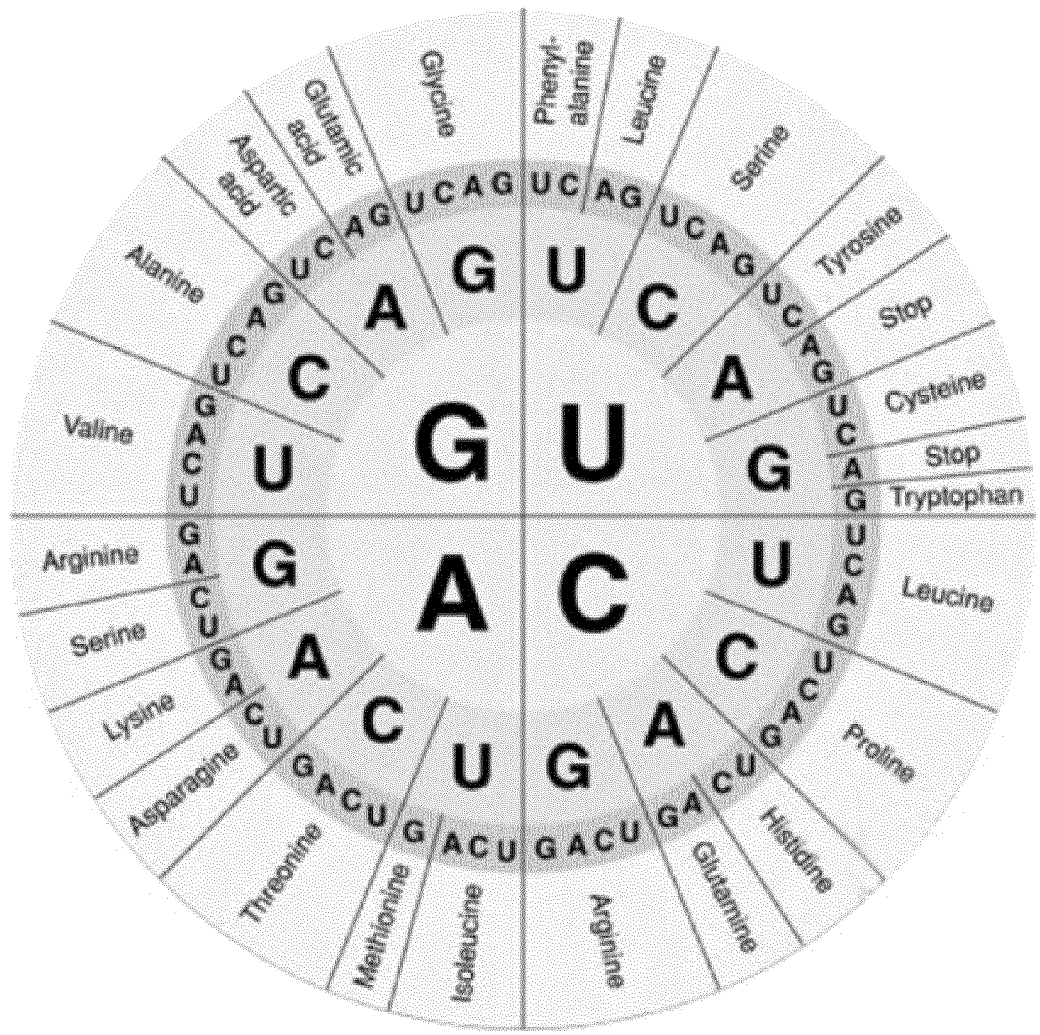
FIG. 1 Scheme of the standard genetic code at the RNA level, with the bases of each codon shown in sense direction, when reading from the inside to the outside.

Unless defined otherwise, all technical and scientific terms used herein have the same meaning as commonly understood by one of ordinary skill in the art (e.g., in cell culture, molecular genetics, nucleic acid chemistry, hybridization techniques and biochemistry). In practicing the present invention, many conventional techniques in molecular biology, microbiology, and recombinant DNA may be used. These techniques are well known and are explained in, for example, Current Protocols in Molecular Biology, Volumes I, II, and III, 1997 (F. M. Ausubel ed.); Sambrook et al., 1989, Molecular Cloning: A Laboratory Manual, Second Edition, Cold Spring Harbor Laboratory Press, Cold Spring Harbor, N.Y.; DNA Cloning: A Practical Approach, Volumes I and II, 1985 (D. N. Glover ed.); Oligonucleotide Synthesis, 1984 (M. L. Gait ed.); Nucleic Acid Hybridization, 1985, (Hames and Higgins); Transcription and Translation, 1984 (Hames and Higgins eds.); Animal Cell Culture, 1986 (R. I. Freshney ed.); Immobilized Cells and Enzymes, 1986 (IRL Press); Perbal, 1984, A Practical Guide to Molecular Cloning; the series, Methods In Enzymology (Academic Press, Inc.); Gene Transfer Vectors for Mammalian Cells, 1987 (J. H. Miller and M. P. Calos eds., Cold Spring Harbor Laboratory); and Methods in Enzymology Vol. 154 and Vol. 155 (Wu and Grossman, and Wu, eds., respectively).

As used herein, the term "about" when used together with a numerical value (e.g., a pH value or a percentage value) is intended to encompass a deviation of 20%, preferably 10%, more preferably 5%, even more preferably of 2%, and most preferably of 1% from that value. When used together with a numerical value it is at the same time to be understood as individually disclosing that exact numerical value as a preferred embodiment in accordance with the present invention.

As used herein, the term "comprising" is to be construed as encompassing both "including" and "consisting of", both meanings being specifically intended, and hence individually disclosed, embodiments in accordance with the present invention.

As used herein, the terms "polypeptide" and "protein" are used interchangeably and refer to a polymer in which the amino acid residues are covalently joined together through peptide (—(C=O)—NH—) and/or disulfide (—S—S—) bonds. "Amino acid residue" is also referred to in short as "amino acid" herein, if not specifically indicated otherwise. The term "polypeptide" in the context of the present invention can refer to monomeric or multimeric, or homomultimeric or heteromultimeric polypeptide molecules. "Polypeptide" can refer to either a full-length naturally-occurring amino acid chain or a "fragment thereof" or "peptide", such as a selected region of the polypeptide that is of interest, or to an amino acid polymer, or a fragment or peptide thereof, which is partially or wholly non-natural. Polypeptides as used herein in particular also encompass any type of antibodies or fragments thereof. "Peptide" as used herein may be short amino acid chains of about 4 amino acids or less. Peptides may also be longer amino acid chains of about 70 amino acids or more. Preferably, peptides are between about 4 to about 70 amino acids in length. A "fragment" of a polypeptide refers to an amino acid sequence that is a portion of a full-length polypeptide.

A polypeptide can be obtained by expression from a polynucleotide which encodes the primary amino acid sequence of said polypeptide. As used herein, "recombinant polypeptides" or "recombinant proteins" are obtainable by recombinant expression from a polynucleotide sequence which encodes said polypeptide or proteins.

Preferred recombinantly expressed polypeptides according to the invention include proteins of pharmaceutical interest. Examples include, without being limited to, Epo, clotting factors such as factor VIII and factor IX, coagulating agents such as hirudin, hormones, including insulin, human and animal growth hormones, follicle stimulating hormone, luteinizing hormone, immunoglobulins and fragments thereof, in particular antibodies and antigen-binding fragments thereof and fusion proteins thereof, alpha-globin, beta-globin, gamma-globin, granulocyte macrophage-colony stimulating factor, tumor necrosis factor, interleukins, macrophage colony stimulating factor, granulocyte colony stimulating factor, mast cell growth factor, tumor suppressor p53, retinoblastoma, interferons, melanoma associated antigen or B7 and any other proteins whose expression is desired, especially in large quantities. Antibodies, antigen-binding fragments and fusion proteins thereof are preferred polypeptides. Antibodies include, but are not limited to, monoclonal antibodies, bispecific antibodies, minibodies, domain antibodies, synthetic antibodies, chimeric antibodies, humanized antibodies, human antibodies, antibody fusions, and antigen-binding fragments thereof. Antibodies, antigen-binding fragments thereof and fusion proteins thereof can be derived from any mammalian source, including but not limited to human, mouse, rat, camelid or rabbit. Antigen-binding fragments of antibodies include, but are not limited to, Fab, a diabody, Fab', F(ab')$_2$, Fv, domain antibodies and single-chain antibodies. Fusion proteins comprise any parts of antibodies fused to another polypeptide, for instance, Fc fusion proteins.

A "polynucleotide" which encodes a polypeptide, as used herein, comprises one or more codons and refers to either a polyribonucleotide (RNA), comprising the bases A, C, G, or U, or a polydeoxyribonucleotide (DNA), comprising the bases A, C, G, T. Polynucleotides can also comprise the base I (inosine, or hypoxanthine) or any modified variant of A, C, G, U, T, I comprising covalently modified nucleotide residues, such as methylated, or de-methylated polynucleotides. A "codon", as used herein, is a triplet of nucleotides having a first, a second and a third base position with respect to the reading frame of the polynucleotide, the codon encoding an amino acid residue according to the genetic code. A polynucleotide encoding a polypeptide may be operably linked to a control sequence, in particular a promoter and/or enhancer that is capable of providing for the expression of the coding sequence by the chosen expression system. These control sequences may be selected to be compatible with the host cell for which the expression system is designed to be used in.

"Expression", as used herein, refers to the process of transcription and/or translation of an encoding polynucleotide as occurring in any naturally occurring cell, host cell, or cell-free transcription and/or translation system. Thus, expression is the production of a polypeptide product from a polynucleotide coding sequence, typically by transcription and/or translation of the coding sequence. Preferably, expression occurs in a cell. Expressed polypeptides may be secreted from the host cell or may accumulate therein. Preferably, expression according to the present invention includes secretion of the polypeptides from the cells. Expression levels may vary, but are advantageously high; about 1%, preferably 10%, 25% or 50% or even more of the total protein produced by the cell may be the expressed polypeptide of interest. A recombinant polypeptide can be prepared by methods employing genetically engineered host cells comprising expression systems well known in the art.

A variety of prokaryotic or eukaryotic in vitro or cellular expression systems or vectors is well known to those skilled in the art and include, but are not limited to chromosomal, episomal and virus-derived expression systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. Generally, any system or vector that is able to maintain, propagate or express a polynucleotide encoding a polypeptide in vitro or in a host cell may be used. The appropriate polynucleotide sequence may be inserted into an expression system by any of a variety of well-known and routine techniques, such as, for example, those set forth in Sambrook et al., 1989, Molecular Cloning: A Laboratory Manual, Second Edition, Cold Spring Harbor Laboratory Press, Cold Spring Harbor, N.Y. Appropriate secretion signals may be incorporated into the desired polypeptide to allow secretion of the translated protein into the lumen of the endoplasmic reticulum, the periplasmic space or the extracellular environment. These signals may be endogenous to the polypeptide or they may be heterologous signals.

As used herein, "host cells" are genetically engineered cells which incorporate expression systems, vectors or portions thereof and are suitable for the production of proteins or polypeptides by recombinant techniques. Representative examples of suitable host cells include bacterial cells, such as Streptococci, Staphylococci, *E. coli, Streptomyces* and *Bacillus subtilis* cells, fungal cells, such as yeast cells and *Aspergillus* cells; insect cells such as *Drosophila* S2 and *Spodoptera* Sf9 cells, other animal cells, or plant cells. Particularly preferred bacterial host cells are *E. coli* cells. Preferred other animal cells comprise, but are not limited to, CHO (Chinese hamster ovary), COS-7 (*Cercopithecus aethiops*, origin-defective SV-40), BHK-21 (Baby hamster kidney fibroblast cells), HEK-293 (Human embryonic kidney), HeLa ("Henrietta Lacks"), HL-60 (Human leukemia), HUVEC (Human umbilical vein endothelial cell), Jurkat, MCF-7 (Michigan Cancer Foundation-7), NIH-3T3 (NIH, 3-day transfer inoculum $3\times10^5$ cells), RenCa (Renal carcinoma), U937, and Vero cells. Particularly preferred in this regard are CHO cells or CHO derived cells (e.g., CHO-DXB11 or, CHO-DG55), which are widely used in the art to express biopharmaceutically useful proteins, such as antibodies and antigen-binding fragments thereof or fusion proteins thereof. An expression system may be introduced into host cells by methods described in standard laboratory textbooks, such as Current Protocols in Molecular Biology, Volumes I, II, and III, 1997 (F. M. Ausubel ed.); Sambrook et al., 1989, Molecular Cloning: A Laboratory Manual, Second Edition, Cold Spring Harbor Laboratory Press, Cold Spring Harbor, N.Y.

Cell-free transcription and/or translation systems can also be employed to produce proteins or polypeptides from a polynucleotide encoding said proteins or polypeptides, wherein DNA is generally used as a template in cell-free coupled transcription/translation systems and RNA is used as a template in cell-free translation systems.

In general, during protein expression, a coding sequence of interest is first transcribed into messenger RNA (mRNA), optionally post-transcriptionally modified, and then translated by the ribosome, using transcription factors and a set of aminoacyl-transfer RNAs (tRNAs). Under normal circumstances, a triplet of three bases within the anticodon loop of an aminoacyl-tRNA forms Watson-Crick base pairs with three bases of its complementary codon, as defined above, within the prokaryotic or eukaryotic ribosome. Each of the $4^3=64$ possible codon triplets is thereby translated into either an amino acid residue (including a start codon) or a translational stop signal, according to the genetic code. The standard genetic code is commonly known and defined herein by the following table and the scheme depicted in FIG. 1.

TABLE 1

The standard genetic code

| 1st base | 2nd base U | | 2nd base C | | 2nd base A | | 2nd base G | | 3rd base |
|---|---|---|---|---|---|---|---|---|---|
| U | UUU | (Phe/F) | UCU | (Ser/S) | UAU | (Tyr/Y) | UGU | (Cys/C) | U |
|   | UUC | Phenylalanine | UCC | Serine | UAC | Tyrosine | UGC | Cysteine | C |
|   | UUA | (Leu/L) | UCA |   | UAA | Stop (Ochre) | UGA | Stop (Opal) | A |
|   | UUG | Leucine | UCG |   | UAG | Stop (Amber) | UGG | (Trp/W) Tryptophan | G |
| C | CUU |   | CCU | (Pro/P) | CAU | (His/H) | CGU | (Arg/R) | U |
|   | CUC |   | CCC | Proline | CAC | Histidine | CGC | Arginine | C |
|   | CUA |   | CCA |   | CAA | (Gln/Q) | CGA |   | A |
|   | CUG |   | CCG |   | CAG | Glutamine | CGG |   | G |
| A | AUU | (Ile) | ACU | (Thr/T) | AAU | (Asn/N) | AGU | (Ser/S) | U |
|   | AUC | Isoleucine | ACC | Threonine | AAC | Asparagine | AGC | Serine | C |
|   | AUA |   | ACA |   | AAA | (Lys/K) | AGA | (Arg/R) | A |
|   | AUG | (Met/M) Methionine* | ACG |   | AAG | Lysine | AGG | Arginine | G |
| G | GUU | (Val/V) | GCU | (Ala/A) | GAU | (Asp/D) | GGU | (Gly/G) | U |
|   | GUC | Valine | GCC | Alanine | GAC | Aspartic acid | GGC | Glycine | C |
|   | GUA |   | GCA |   | GAA | (Glu/E) | GGA |   | A |
|   | GUG |   | GCG |   | GAG | Glutamic acid | GGG |   | G |

*AUG codes for Met and can also serve as an initiation site

Other genetic codes are also known in the art which slightly differ from the standard genetic code, such as the vertebrate mitochondrial code, the yeast mitochondrial code, as well as other mitochondrial, nuclear, and plastid genetic codes, see Osawa et al. Microbiol Rev. 1992, 56(1):229-64; Jukes and Osawa, Comp Biochem Physiol B. 1993, 106(3): 489-94. The methods of the present invention preferably use the standard genetic code, but can also be adapted to such variant genetic codes.

Transcription mechanisms as well as translational mechanisms are not error free. As compared, e.g., to the high-fidelity, eukaryotic DNA-dependent DNA polymerase replication machinery, which usually exhibits an error rate of about $10^{-8}$ to $10^{-10}$ per base pair due to extensive proofreading (Kunkel and Bebenek, Annu Rev Biochem. 2000; 69:497-529), the error rates of transcription and translation are several magnitudes higher. Error rates of transcription are reported to be about $10^{-5}$ (Sydow and Cramer, Curr Opin Struct Biol. 2009, 19(6):732-9) per base. Ribosome-dependent translation takes place with an error rate of about $10^{-3}$ to $10^{-4}$ per amino acid residue (Loftfield and Vanderjagt, Biochem. J. 1972, 128, 1353-1356; Parker et al., Proc Natl Acad Sci USA 1978, 75(3):1091-5). At such frequency, proteins or polypeptides comprising at least one misincorporated amino acid residue are detectable by state-of-the art analytical methods, e.g., mass spectrometric methods.

Transcriptional errors are the result of non-Watson-Crick base mismatches at the DNA/RNA level and lead to one or more nucleotide substitutions, or base differences within the transcript mRNA. If this one or more base difference happens to occur within the coding region of a mRNA polynucleotide and is not corrected by proofreading mechanisms (reviewed in Sydow and Cramer, Curr Opin Struct Biol. 2009, 19(6):732-9), the erroneous codon within the mRNA transcript can pair with a "wrong" aa-tRNA that carries a non-native amino acid during translation. Whether or not the transcriptional error will be translated into a misincorporated amino acid residue within the polypeptide obtained by expression, depends on the exact position of such transcription error within the codon, i.e. at the first, the second, or the third position of the codon. Of note, the third position of a codon, also termed the "wobble" position, inherently accounts for the degeneracy of the genetic code. According to the standard genetic code, transcriptional errors at the third (or wobble) position of codons for Gly, Ala, Val, Thr, Arg, Pro, Leu, Ser would be silent at the translational level.

Translational errors are the result of an RNA/RNA non-Watson-Crick base-base mismatch between the anticodon of an aminoacyl-tRNA (in its ribosome-bound state) and a codon of the mRNA transcript to be translated. If the aminoacyl-tRNA differs in its aminoacyl residue from the translation of the mismatched codon according to the genetic code, an amino acid residue misincorporation occurs.

"Watson-Crick base pairs" are G-C, A-T or A-U base pairs. "Non-Watson-Crick base mismatch" as used herein generally refers to any base pair that is not a Watson-Crick base pair. Such mismatched base pair is designated "N*N" ("N" being any nucleotide) Most common and, therefore, preferred non-Watson-Crick base mismatches are:

a. a C*A mismatch between a DNA template strand and an mRNA being transcribed from said DNA template strand; or a G*U mismatch between the mRNA codon and an anticodon of an amino-acyl tRNA during translation, as described in Gautheret et al. RNA 1995, 1(8):807-14. These mismatches result in a base difference of G to A (G→A) within the genetic code.

b. an A*C mismatch between a DNA template strand and an mRNA being transcribed from said DNA template strand; or a U*G mismatch between the mRNA codon and an anticodon of an amino-acyl tRNA during translation, as described in Gautheret et al. RNA 1995, 1(8):807-14. These mismatches result in a base difference of U to C (U→C) within the genetic code.

c. an A*A mismatch between a DNA template strand and an mRNA being transcribed from said DNA template strand; or an U*U mismatch between the mRNA codon and an anticodon of an amino-acyl tRNA during translation, as described in Baeyens et al. Nat Struct Biol 1995, 2(1):56-62. These mismatches result in a base difference of U to A (U→A) within the genetic code.

Non-Watson-Crick base mismatches can have a profound impact on the quality of a polypeptide product, resulting in low level sequence variants in the product which are detectable by highly sensitive analytical techniques, such as liquid chromatography mass spectrometry (LC-MS), as described further below.

The term "low level sequence variant(s)" as used herein refers to one or more variants of a polypeptide encoded by a polynucleotide according to the genetic code, wherein the variant(s) differ(s) in at least one amino acid residue from the primary amino acid sequence of the encoded polypeptide due to amino acid residue misincorporation resulting from at least one non-Watson-Crick base mismatch as defined above. Low level sequence variants may comprise one amino acid residue misincorporation, or 2, 3, 4, 5, 6, 7, 8, 9, 10, 11, 12, 13, 14, 15, 16, 17, 18, 19, 20, or more misincorporations, depending on the length and primary sequence of the polypeptide, or the occurrence and/or frequency of codons susceptible to amino acid residue misincorporation(s) within the coding sequence of the polynucleotide, respectively. The concentration of low level sequence variants within a mixture of polypeptides obtained by expression of the polynucleotide in a cell is generally low in relation to the encoded polypeptide. Typically, a given amino acid residue misincorporation is present in less than 10%, less than 5%, less than 1%, less than 0.5%, less than 0.1%, or less than 0.02% of the total molar amount of the expressed polypeptide. Preferably, the amino acid residue misincorporation is present in less than 0.5%, and more preferably in less than 0.1% of the total molar amount of the expressed polypeptide. The "encoded polypeptide", not comprising any amino acid residue misincorporation is also termed "correct", "main" or "native" polypeptide herein, as opposed to low level sequence variants.

The term "amino acid residue misincorporation", as used in the context of the present invention, generally refers to an amino acid residue being incorporated into a polypeptide, which is not encoded by the codon at the corresponding position of the encoding polynucleotide according to the genetic code. The knowledge of the molecular mechanism(s) leading to codon dependent amino acid misincorporations has only emerged recently (Yu et al., Anal. Chem. 2009, 81, 9282-9290). An amino acid residue misincorporation is the result of at least one non-Watson-Crick base mismatch, as defined above, during transcription or translation at one or more of the first, second, or the third positions of at least one codon within the encoding polynucleotide. Some amino acid residues or their one or more possible codons are more susceptible to amino acid residue misincorporation than others. Codons which are susceptible to amino acid residue misincorporation are an object of the methods of the present invention.

A codon being "susceptible to amino acid residue misincorporation(s)" is generally a codon which, if altered by at least one base difference due to non-Watson-Crick base mismatches during transcription or translation, would encode another amino acid residue. Preferably, codons susceptible to amino acid misincorporation(s) are codons which would encode another amino acid residue, if altered by at least one base difference due to a non-Watson-Crick base mismatch at the first or the second base position. Tables 2 and 3 list particularly preferred codons being susceptible to amino acid residue misincorporation(s). Accordingly, Tables 2 and 3 list preferred amino acid residues encoded by codons being susceptible to amino acid misincorporation(s). Upon expression of a polynucleotide comprising at least one codon being susceptible to amino acid residue misincorporation(s) in any appropriate expression system introduced in any cell, host cell or in vitro transcription and/or translation system as defined above, low level sequence variants of the polypeptide encoded by said polynucleotide, which differ in at least the amino acid residue encoded by said codon will be detectable by appropriate detection methods as described herein and as known from the prior art.

The "degree" of amino acid misincorporation refers to the rate or frequency of the occurrence of said amino acid residue misincorporation per amino acid position within a polypeptide.

The "type" of amino acid misincorporation refers to the identity of the amino acid residue being misincorporated in place of the native amino acid residue which is encoded by the polynucleotide according to the genetic code.

Generally, any polypeptide being used for therapy in a patient may elicit an immune response to a higher or lesser extent, according to its immunogenic potential. The term "immunogenic potential", as used in the context of the present invention, refers to the capability of a polypeptide to elicit an immune response directed against said polypeptide. The term "immune response" as used herein generally refers to a cellular or humoral immune response of a subject (host) that recognizes an antigen presented by the polypeptide (foreign). Specifically, immunogenic potential resides in the presence of T-cell epitopes in a polypeptide, which is bound by MHC Type II/HLA complex. Accordingly, immunogenic potential can be determined by the capability of the polypeptide to elicit the formation of antibodies specific for an antigen comprised in the polypeptide. If the polypeptide is a biopharmaceutical polypeptide, such antibodies are also known as anti-drug antibodies (ADA) in the art. The immunogenic potential of a polypeptide or fragments thereof can be assessed in vitro, in vivo, or in silico. In silico tools for determining the immunogenic potential of polypeptides or fragments thereof are described in the prior art, e.g., Roque-Navarro et al. Hybrid Hybridomics 2003, 22(4):245-57; Tangri et al. Current Medicinal Chemistry 2002, 9, 2191-2199; Mateo et al. Hybridoma 2000, 19(6):463-71; De Groot et al. Vaccine 2009, 27 5740-5747, incorporated herein by reference in their entirety. Suitable in vitro assays for testing the immunogenic potential of an entire protein or a peptide representing a potential epitope include, but are not limited to, an MHC II binding assay or T-cell assay. Suitable in vivo assays for testing the immunogenic potential of a an entire protein or a peptide representing a potential epitope include, but are not limited to, a transgenic (e.g. expressing the human HLA gene products) animal model testing its immunogenic potential, as disclosed, e.g., by De Groot & Moise Curr Opin Drug Discov Devel 2007, 10(3):332-40, incorporated herein by reference in its entirety.

Expressed polypeptides and recombinant polypeptides can generally be purified from a culture of host cells or from an in vitro expression system according to routine practice. However, notwithstanding current purification protocols and state-of-the-art instrumentation, a polypeptide so purified may contain low level sequence variants as defined above. The degree and type of amino acid residue misincorporation(s) within such low level sequence variants can be determined, e.g., by mass spectrometric methods.

Specifically, the methods of the present invention may comprise a step of using liquid chromatography-mass spectrometry, or high pressure liquid chromatography-mass spectrometry, referred to as "LC-MS", or "HPLC-MS" herein. In particular, LC-MS includes tandem LC-MS, also referred to as "LC-MS/MS". Preferably, LC-MS is carried out using reverse phase nano-LC-MS (RP-nano-LC-MS) technology. This allows for the use of a small sample volume and the possibility to operate with high throughput, such as in a 96-well plate sample preparation. It also provides high sensitivity.

As used herein "nano-LC" or nano-HPLC, including RP-nano-LC or RP-nano-HPLC, is characterized by a decreased inner diameter of the columns that are used for LC (10-150 μm) and smaller flow-rates (10-1000 nl/min) compared to conventional LC or HPLC, respectively. This down-scaling results in high plate counts of the nano-LC system and the ability to analyze proteinaceous samples in the low femtomole and subfemtomole ranges (Chervet et al., Analytical Chemistry 1996, 68:1507-12, incorporated herein by reference in its entirety). Consistent with the understanding and common general knowledge in the field of liquid chromatography, it will be appreciated that in accordance with the invention nano-LC and nano-HPLC are suitable and intended forms of LC and HPLC, respectively, for the purposes of the present invention; and that RP-nano-LC and RP-nano-HPLC are suitable and intended forms and even preferred forms of RP-LC and RP-HPLC, respectively. The same applies to the likewise well-known and established techniques of micro-LC and capillary-LC, or RP-micro-LC and RP-capillary-LC, which for the purposes of the present invention are suitable and intended forms of LC, and RP-LC, respectively. Where the terms LC, HPLC, LC-MS or HPLC-MS is used herein, this also encompasses their preferred embodiments, nano-LC, nano-HPLC, nano-LC-MS or nano-HPLC-MS and their reverse phase forms.

For the purposes of the present invention, a "mobile phase" of RP-LC or RP-HPLC is preferably a gradient of an organic modifier (e.g., acetonitrile or methanol) in water, with an ionic modifier that controls the pH and ionization state or acts as an ion pairing reagent. Anionic ion-pair reagents (e.g., trifluoroacetic acid (TFA)) bind to protonated basic groups of peptides. The addition of 0.1% TFA acidifies the eluent which causes the carboxylic groups of peptides and proteins to become protonated, resulting in a larger hydrophobicity of the molecules. Cationic ion-pairing reagents (e.g., triethylammonium ions) bind to ionized carboxyl groups of peptides ("*Protein Liquid Chromatography*", Journal of Chromatography Library, vol. 61, edited by Kastner M, Elsevier Science B.V., 2000, page 153, incorporated herein by reference in its entirety). Diethylamine (DEA) can also be used as an ion pairing reagent (Melmer et al., Journal of Chromatography A (2011), Volume: 1218(1): 118-123). For normal phase or HILIC chromatography, a suitable mobile phase consists for example of 60 mMol ammonium formate in 75% acetonitrile (mobile phase A) and 115 mMol ammonium formate in 54% acetonitrile (mobile phase B) (Melmer et al., Anal Bioanal Chem (2010), Volume 398: 905-914, incorporated herein by reference in its entirety).

As used herein, "ion trap mass spectrometry" is an arrangement in which ions with a desired range of quotients mass/charge are first made to describe stable paths under the effect of a high-frequency electric quadrupole field, and are then separated and presented to a detector by adjusting the field so as to selectively induce path instability according to their respective mass/charge ratios e.g., quadrupole ion trap. Sensitivity of the methods of the invention can be improved by using more sensitive nano ESI sources.

As used herein, "extracted ion chromatography" refers to an LC-MS experiment, in which data for essentially the entire mass range of analytes/ions of interest is collected, and subsequently one or more m/z values of one or more analyte are recovered ('extracted') from the spectrogram, thereby providing the "extracted ion chromatogram" (EIC).

The EIC is created by plotting the intensity of the signal observed at a chosen m/z value or set of values in a series of mass spectra recorded as a function of retention time.

Method for Optimizing a Coding Sequence

Described and claimed herein in accordance with the invention is a method for optimizing the coding sequence of a polynucleotide that encodes a polypeptide, the method comprising: (a) identification of at least one codon within said coding sequence which is susceptible to amino acid residue misincorporation at a position within the encoded polypeptide that corresponds to said codon; (b) identification of at least one codon within said coding sequence which is susceptible to amino acid residue misincorporation at a position within the encoded polypeptide that corresponds to said codon and selecting an alternative codon to the at least one codon so as to change the degree or type of amino acid residue misincorporation; (c) changing at least one codon within said coding sequence to an alternative codon, wherein said at least one codon is susceptible to amino acid residue misincorporation at a position within the encoded polypeptide that corresponds to said codon, so as to change the degree or type of amino acid residue misincorporation; or (d) identification of at least one codon within said coding sequence which is susceptible to amino acid residue misincorporation at a position within the encoded polypeptide that corresponds to said codon and changing said codon to an alternative codon so as to change the degree or type of amino acid residue misincorporation.

In one embodiment of the method of the invention, the amino acid residue misincorporation is the result of at least one non-Watson-Crick base mismatch during transcription or translation, as defined above. The at least one non-Watson-Crick base mismatch during translation or transcription results in a base difference within said at least one codon according to the genetic code. Thus, in some embodiments of all aspects of the invention, the base difference is selected from the group consisting of A→C, A→G, C→A, C→U, G→A, G→C, G→U, U→A, U→C, and U→G. In a preferred embodiment, the base difference is selected from the group consisting of G→A, U→C, and U→A. In particularly preferred embodiments, the base difference with regard to the position within said at least one codon is selected from the group consisting of G1→A, G2→A, U1→A, U1→C, U2→A, U2→C.

Table 2 summarizes which amino acid misincorporation (s) could result from the respective codon(s) encoding the intended, "native" amino acid to be incorporated into the protein sequence.

TABLE 2

Amino acid misincorporations

| Native amino acid | codon used | misincorporation |
| --- | --- | --- |
| Glycine | GGC or GGU | Aspartate |
|  | GGG or GGA | Glutamate |
|  | GGG or GGA | Arginine |
|  | GGC or GGU | Serine |
| Alanine | all 4 codons | Threonine |
| Serine | AGC or AGU | Asparagine |
|  | UCU, UCC, UCA or UCG | Proline |
|  | UCU, UCC, UCA or UCG | Threonine |

TABLE 2 -continued

Amino acid misincorporations

| Native amino acid | codon used | misincorporation |
|---|---|---|
| Arginine | CGG or CGA | Glutamine |
| | CGU or CGC | Histidine |
| | AGG or AGA | Lysine |
| Valine | GUA, GUU, GUC | Isoleucine |
| | GUG | Methionine |
| | all 4 codons | Alanine |
| | GUC or GUU | Aspartate |
| | GUG or GUA | Glutamate |
| Isoleucine | AUA | Lysine |
| | AUC or AUU | Asparagine |
| | all 3 codons | Threonine |
| Methionine | AUG | Lysin |
| | AUG | Threonine |
| Leucine | UUA or UUG | Serine |
| | CUU or CUC | Histidine |
| | CUA or CUG | Glutamine |
| | UUA | Isoleucine |
| | UUG | Methionine |
| Phenylalanine | all 2 codons | Serine |
| | all 2 codons | Leucine |
| | all 2 codons | Tyrosine |
| | all 2 codons | Isoleucine |
| Tyrosine | all 2 codons | Histidine |
| | all 2 codons | Asparagine |
| Cysteine | all 2 codons | Tyrosine |
| | all 2 codons | Arginine |
| | all 2 codons | Serine |
| Tryptophan | UGG | Arginine |

From Table 2 it can be concluded that for some of the amino acids different codons lead to different amino acids being misincorporated into the polypeptide sequence giving rise to a number of protein sequences, termed low level sequence variants herein, which are different in sequence from the encoded (i.e. intended/native) sequence.

Thus, in an embodiment of the invention, the native amino acid residues listed in Table 2 are encoded by the at least one codon being susceptible to amino acid residue misincorporation. In some embodiments, the at least one codon being susceptible to amino acid residue misincorporation is preferably selected from the group consisting of AGA, AGC, AGG, AGU, AUA, AUC, AUG, CGA, CGC, CGG, CGU, CUA, CUC, CUG, CUU, GCA, GCC, GCG, GCU, GGA, GGC, GGG, GGU, GUA, GUC, GUG, GUU, UAC, UAU, UCA, UCC, UCG, UCU, UGC, UGG, UGU, UUA, UUC, UUG, and UUU at the RNA level, or their corresponding codons at the DNA level. In another embodiment of the invention, the at least one codon being susceptible to amino acid residue misincorporation is selected from the group consisting of AGA, AGC, AGG, AGU, AUA, AUC, CGA, CGC, CGG, CGU, CUA, CUC, CUG, CUU, GCA, GCC, GCG, GCU, GGA, GGC, GGG, GGU, GUA, GUC, GUG, GUU, UAC, UAU, UCA, UCC, UCG, UCU, UGC, UGU, UUA, UUC, UUG, and UUU at the RNA level, or their corresponding codons at the DNA level. In another embodiment, the at least one codon being susceptible to amino acid residue misincorporation encodes an amino acid residue selected from the group consisting of Gly, Ala, Ser, Arg, Val, Ile, Leu, Met, Phe, Tyr, Cys, and Trp. In a preferred embodiment, the at least one codon being susceptible to amino acid residue misincorporation is selected from the group consisting of AGA, AGC, AGG, AGU, AUA, AUC, AUG, CGA, CGC, CGG, CGU, CUA, CUC, CUG, CUU, GGA, GGC, GGG, GGU, GUA, GUC, GUG, GUU, UCA, UCC, UCG, UCU, UUA, UUG. In a more preferred embodiment, the at least one codon being susceptible to amino acid residue misincorporation is selected from the group consisting of AGA, AGC, AGG, AGU, AUA, AUC, CGA, CGC, CGG, CGU, CUA, CUC, CUG, CUU, GGA, GGC, GGG, GGU, GUA, GUC, GUG, GUU, UCA, UCC, UCG, UCU, UUA, UUG. In a preferred embodiment, the at least one codon being susceptible to amino acid residue misincorporation encodes an amino acid residue selected from the group consisting of Gly, Ser, Arg, Val, Ile, Leu and Met. In a more preferred embodiment, the at least one codon being susceptible to amino acid residue misincorporation encodes an amino acid residue selected from the group consisting of Gly, Ser, Arg, Val, Ile and Leu.

In another preferred embodiment, at the position corresponding to the native residue of the polypeptide encoded by the at least one codon being susceptible to amino acid residue misincorporation, Asp is misincorporated in place of Gly; Glu is misincorporated in place of Gly; Arg is misincorporated in place of Gly; Ser is misincorporated in place of Gly; Asp is misincorporated in place of Ser; Gln is misincorporated in place of Arg; His is misincorporated in place of Arg; Lys is misincorporated in place of Arg; Ile is misincorporated in place of Val; Met is misincorporated in place of Val; Ser is misincorporated in place of Leu; Pro is misincorporated in place of Ser; Glu is misincorporated in place of Val; Asp is misincorporated in place of Val; Lys is misincorporated in place of Ile; Asp is misincorporated in place of Ile; Lys is misincorporated in place of Met; His is misincorporated in place of Leu; Gln is misincorporated in place of Leu; Ile is misincorporated in place of Leu; or Met is misincorporated in place of Leu.

In a more preferred embodiment, (a) the at least one codon is GGC or GGU and aspartate is misincorporated in place of glycine; (b) the at least one codon is GGG or GGA and glutamate is misincorporated in place of glycine; (c) the at least one codon is GGG or GGA and arginine is misincorporated in place of glycine; (d) the at least one codon is GGC or GGU and serine is misincorporated in place of glycine; (e) the at least one codon is AGC or AGU and asparagine is misincorporated in place of serine; (f) the at least one codon is CGG or CGA and glutamine is misincorporated in place of arginine; (g) the at least one codon is CGU or CGC and histidine is misincorporated in place of arginine; (h) the at least one codon is AGG or AGA and lysine is misincorporated in place of arginine; (i) the at least one codon is GUA, GUU, or GUC and isoleucine is misincorporated in place of valine; (j) the at least one codon is GUG and methionine is misincorporated in place of valine; (k) the at least one codon is UUA or UUG and serine is misincorporated in place of leucine; (l) the at least one codon is UCU, UCC, UCA or UCG and proline is misincorporated in place of serine; (m) the at least one codon is GUG or GUA and glutamate is misincorporated in place of valine; (n) the at least one codon is GUC or GUU and aspartate is misincorporated in place of valine; (o) the at least one codon is AUA and lysine is misincorporated in place of isoleucine; (p) the at least one codon is AUC or AUA and asparagine is misincorporated in place of isoleucine; (q) the at least one codon is AUG and lysine is misincorporated in place of methionine; (r) the at least one codon is CUU or CUC and histidine is misincorporated in place of leucine; (s) the at least one codon is CUA or CUG and glutamine is misincorporated in place of leucine; (t) the at least one codon is UUA and isoleucine is misincorporated in place of leucine; or (u) the at least one codon is UUG and methionine is misincorporated in place of leucine.

In some embodiments of the invention, if any of the above at least one codons being susceptible to amino acid residue misincorporation is identified within the polynucleotide, an alternative codon alternative codon is selected or said at least one codon is changed, so as to change the degree or type of amino acid residue misincorporation. In some embodiments, the alternative codon is itself susceptible to amino acid misincorporation(s). In some embodiments, the alternative codon is not susceptible to amino acid misincorporation(s).

In some embodiments, the amino acid residue misincorporation is present in less than about 1%, less than about 0.5%, less than about 0.2%, less than about 0.1% or less than about 0.01% of the total molar amount of the polypeptide. In other words, the degree or rate of an amino acid misincorporation due to non-Waston-Crick base mismatch within the at least one codon is less than about 1%, less than about 0.5%, less than about 0.2%, less than about 0.1% or less than about 0.02%. Typically, the degree or rate of an amino acid misincorporation is up to about 0.5%. Most typically, the degree or rate of misincorporation per amino acid residue position is up to about 0.2%.

As will be understood, in some embodiments, a polypeptide comprises exactly one amino acid misincorporation over its entire length. In other embodiments, a polypeptide comprises 2, 3, 4, 5, 6, 7, 8, 9, 10, 11, 12, 13, 14, 15, 16, 17, 18, 19, 20, or more misincorporations, depending on the length and encoding polynucleotide sequence.

Reverse Engineering

The inventors have uncovered, using highly sensitive analytical techniques, that low level sequence variants occurring due to misincorporation of amino acid residues during translation and/or transcription can serve to identify at least one codon encoding such at least one misincorporated amino acid residue. Accordingly, the present invention provides a method of optimizing the coding sequence of a polynucleotide for use in reverse-engineering. In this aspect of the invention, the method for optimizing the coding sequence of a polynucleotide generally comprises determining the degree or type of amino acid residue misincorporation found in either the polypeptide obtained by expression of said polynucleotide to be optimized; and/or a polypeptide obtainable by expression of a second polynucleotide which encodes the same polypeptide but differs in said at least one codon from the polynucleotide to be optimized. According to the invention, the at least one differing codon within the second polynucleotide is not known before the method of the invention is put into practice. In some embodiments, all codons within the second polynucleotide are not known before the method of the invention is put into practice. According to this aspect of the invention, said second polynucleotide or the coding sequence of said second polynucleotide is not available or not fully available, but only the polypeptide obtainable by expression of said second polynucleotide is available, e.g. commercially available, wherein that polypeptide comprises low level sequence variants comprising one or more amino acid misincorporations.

By way of determining the presence or absence, degree or type of an amino acid residue misincorporation within a low level sequence variant of a polypeptide, at least one codon coding for this amino acid residue can be identified (reverse engineering), since a specific amino acid misincorporation is specific for such codon. Preferably, at least one codon coding for Gly, Ser, Arg, Val, Ile and Leu can be identified when having determined the degree or type of misincorporation in the low-level sequence variant.

In one embodiment, said alternative codon is selected, or said at least one codon is changed, respectively, so as to match the degree or type of amino acid residue misincorporation found within a polypeptide obtainable by expression of a second polynucleotide which encodes the same polypeptide but differs in said at least one codon from the polynucleotide to be optimized. Preferably, the method of the invention comprises determining the degree or type of amino acid residue misincorporation found in a polypeptide obtainable by expression of a second polynucleotide which encodes the same polypeptide but differs in said at least one codon from the polynucleotide to be optimized, and wherein said alternative codon is selected, or said at least one codon is changed, respectively, so as to match the degree or type of amino acid residue misincorporation found within said polypeptide obtainable by expression of a second polynucleotide which encodes the same polypeptide but differs in said at least one codon from the polynucleotide to be optimized. More preferably, the method of the invention comprises identification of at least one codon within said coding sequence which is susceptible to amino acid residue misincorporation at a position within the encoded polypeptide that corresponds to said codon and changing said codon to an alternative codon so as to change the degree or type of amino acid residue misincorporation, wherein said identification step comprises determining the degree or type of amino acid residue misincorporation found in a polypeptide obtainable by expression of a second polynucleotide which encodes the same polypeptide but differs in said at least one codon from the polynucleotide to be optimized, and wherein said alternative codon is selected, or said at least one codon is changed, respectively, so as to match the degree or type of amino acid residue misincorporation found within said polypeptide obtainable by expression of said second polynucleotide which encodes the same polypeptide but differs in said at least one codon from the polynucleotide to be optimized.

Accordingly, it is possible to reverse-engineer at least one codon of an unknown (i.e., the second) polynucleotide sequence, and optimize the known sequence by changing said at least one codon or selecting said alternative codon so that a polypeptide expressed from the so optimized polynucleotide will not differ, or will not significantly differ, in respect of said misincorporation from the polypeptide expressed from the unknown second polynucleotide. In some embodiments, the alternative codon is itself susceptible to amino acid misincorporation(s). In some embodiments, the alternative codon is not susceptible to amino acid misincorporation(s). This method can be independently carried out for each codon susceptible to amino acid misincorporation within the open reading frame of a polynucleotide to be optimized. Engineering the so optimized polynucleotide and transfer into an expression system then allows achieving expression of the polypeptide in a host cell or in an in vitro expression system in such a manner that the pattern, or "fingerprint", of accompanying low level sequence variants of the expressed polypeptide is similar, or identical, to that of the polypeptide expressed from the unknown second polynucleotide.

The identification of the at least one codon can be readily done according the following table, termed "reverse engineering matrix".

TABLE 3

Reverse engineering matrix

| Amino acid residue | Low-level sequence variant | Encoding codon |
|---|---|---|
| Glycine | Aspartate | GGC or GGU |
| Glycine | Glutamate | GGG or GGA |
| Glycine | Arginine | GGG or GGA |
| Glycine | Serine | GGC or GGU |
| Serine | Asparagine | AGC or AGU |
| Arginine | Glutamine | CGG or CGA |
| Arginine | Histidine | CGU or CGC |
| Arginine | Lysine | AGG or AGA |
| Valine | Isoleucine | GUA, GUU, GUC |
| Valine | Methionine | GUG |
| Leucine | Serine | UUA or UUG |
| Serine | Proline | UCU, UCC, UCA or UCG |
| Valine | Glutamate | GUG or GUA |
| Valine | Aspartate | GUC or GUU |
| Isoleucine | Lysine | AUA |
| Isoleucine | Asparagine | AUC or AUA |
| Methionine | Lysine | AUG |
| Leucine | Histidine | CUU or CUC |
| Leucine | Glutamine | CUA or CUG |
| Leucine | Isoleucine | UUA |
| Leucine | Methionine | UUG |

Accordingly, a skilled person will understand from Table 3 which codon is to be changed and/or which alternative codon is to be selected according to the method of the invention. For example, if the presence of at least one Gly→Asp misincorporation is determined within a low level sequence variant of a given polypeptide (expressed from an unknown, second polynucleotide), it can be taken from the third row of Table 3 that either GGC or GGU should be selected as an alternative codon to the at least one codon within the coding sequence of the polynucleotide to be optimized so as to match the degree or type of Gly→Asp misincorporation upon expression.

In an alternative example, if the presence of at least one Gly→Glu misincorporation is determined within a low level sequence variant of a given polypeptide (expressed from an unknown, second polynucleotide), it can be taken from the third row of Table 3 that either GGG or GGA should be selected as an alternative codon to the at least one codon within the coding sequence of the polynucleotide to be optimized so as to match the degree or type of Gly→Glu misincorporation upon expression.

As will be understood from Table 3, in preferred embodiments of this aspect of the invention, the alternative codon to be selected, or said at least one codon to be changed is selected from the group consisting of AGA, AGC, AGG, AGU, AUA, AUC, AUG, CGA, CGC, CGG, CGU, CUA, CUC, CUG, CUU, GGA, GGC, GGG, GGU, GUA, GUC, GUG, GUU, UCA, UCC, UCG, UCU, UUA, UUG. In a more preferred embodiment, the at least one codon to be changed is preferably selected from the group consisting of AGA, AGC, AGG, AGU, AUA, AUC, CGA, CGC, CGG, CGU, CUA, CUC, CUG, CUU, GGA, GGC, GGG, GGU, GUA, GUC, GUG, GUU, UCA, UCC, UCG, UCU, UUA, UUG.

The principle of reverse engineering is further exemplified in Example 1.

Codon Optimization

As will be understood, one or more amino acid misincorporations within a polypeptide can alter the immunogenic potential of a polypeptide. In this aspect, the method of codon optimization of the invention can be used to alter the immunogenic potential of any polypeptide being expressed from an encoding polynucleotide.

The inventors have recognized that the amino acid sequence of an expressed polypeptide can vary in a considerable portion of its primary sequence, leading to low level sequence variants comprising at least one amino acid misincorporation resulting from mistranscriptional and/or mistranslational events. Such low level sequence variants can exhibit an altered immunogenic potential as compared to the native polypeptide not comprising any amino acid residue misincorporation. Codon selection based on the immunogenic potential of the misincorporated amino acid might further lower the immunogenic potential of the protein drug. Accordingly, in a preferred embodiment of the method of the invention, codon optimization is used to reduce the immunogenic potential of biopharmaceuticals (CORIP). In this preferred embodiment of the invention, the at least one amino acid residue misincorporation results in an increase in immunogenic potential of said polypeptide, as defined above. If the polypeptide is used in therapy in a subject, an increase in immunogenic potential may, e.g., result in the formation of anti-drug antibodies. Formation of anti-drug antibodies (ADA) following repeated administration of therapeutic polypeptides can have profound consequences for a subject, ranging in impact from loss of efficacy to life threatening conditions. Thus, in a preferred embodiment the method of codon optimization of the invention comprises the selection of an alternative codon, or the change of said at least one codon, respectively, thereby resulting in a decrease in immunogenic potential of the polypeptide. More preferably, in this aspect of the invention, the method comprises identification of at least one codon within said coding sequence which is susceptible to amino acid residue misincorporation at a position within the encoded polypeptide that corresponds to said codon and changing said codon to an alternative codon so as to change the degree or type of amino acid residue misincorporation, wherein the selection of said alternative codon, or the change of said at least one codon, respectively, results in a decrease in immunogenic potential of said polypeptide. This is useful in applications, where a decreased immunogenic potential of a polypeptide is desired, e.g., when developing a therapeutic polypeptide, and wherein the polypeptide as originally provided exhibits an intolerable immunogenicity and/or immunogenic potential.

In another embodiment of the invention, the amino acid residue misincorporation results in a decrease in immunogenic potential of said polypeptide, as defined above. In this embodiment, the method of codon optimization of the invention comprises the selection of an alternative codon, or the change of said at least one codon, respectively, thereby resulting in an increase in immunogenic potential of the polypeptide. This is useful in applications, where an enhanced or increased immune response in a subject is actually desired, e.g., in a recombinantly produced vaccine.

In one embodiment, the immunogenic potential of a polypeptide comprising at least one amino acid misincorporation is assessed by individually changing each amino acid listed in Table 2 with the respective misincorporation due to non-Watson-Crick base mismatches, and subjecting the resulting polypeptide sequence to in silico prediction of T helper cell epitopes using computational tools described in the prior art, such as Bryson et al., 2010; De Groot & Moise, 2007; Perry et al., 2008, as defined above, optionally in comparison to the unaltered, native polypeptide sequence, using the same tools. The at least one codon encoding the changed amino acid residue which shows the least immunogenic potential when changed within the polypeptide sequence is selected for optimizing the polynucleotide sequence encoding the polypeptide. In a further embodiment, the in silico prediction of T helper cell epitopes is confirmed by an in vitro assay, including an MHC II binding assay, or by an in vivo assay, including, but not limited to, a T cell assay.

In another embodiment, the immunogenic potential of a polypeptide comprising at least one amino acid misincorporation is assessed by individually mutating each amino acid listed in Table 2 with the respective misincorporation due to non-Watson-Crick base mismatches by standard molecular biology techniques, and subjecting the resulting polypeptide to a suitable in vitro assays, as defined above, optionally in comparison to the unaltered, native polypeptide sequence, using the same tools. The at least one codon encoding the mutated amino acid residue which shows the least immunogenic potential when mutated within the polypeptide sequence is selected for optimizing the polynucleotide sequence encoding the polypeptide. CORIP is exemplified in detail in Example 3.

All publications as cited herein are incorporated herein by reference in their entirety. The invention is further illustrated by the following Figures and Examples, which are not to be considered as being limiting for the scope of protection conferred by the claims of the present application.

EXAMPLES

Example 1—Low Level Sequence Variants

LC-MS/MS analysis of a given polypeptide according to standard practice reveals the native peptide STSGGTAAL-GCLVK (SEQ ID. No. 1) and three low-level sequence variants. At the three Gly positions of the native peptide, sequence variants each comprising a Gly to Glu (G→E), or a Gly to Asp (G→D) amino acid misincorporation are identified at a relative abundancy of about 0.02% of the total amount of peptide), as shown in Table 4.

TABLE 4

|  | sequence | Relative abundancy |
| --- | --- | --- |
| Native peptide | STSGGTAALGCLVK (SEQ ID. No. 1) | ~99.94% |
| Sequence variant 1 | STSEGTAALGCLVK (SEQ ID. No. 2) | ~0.02% |
| Sequence variant 2 | STSGDTAALGCLVK (SEQ ID. No. 3) | ~0.02% |

TABLE 4-continued

|  | sequence | Relative abundancy |
| --- | --- | --- |
| Sequence variant 3 | STSGGTAALDCLVK (SEQ ID. No. 4) | ~0.02% |

Figure 2A:
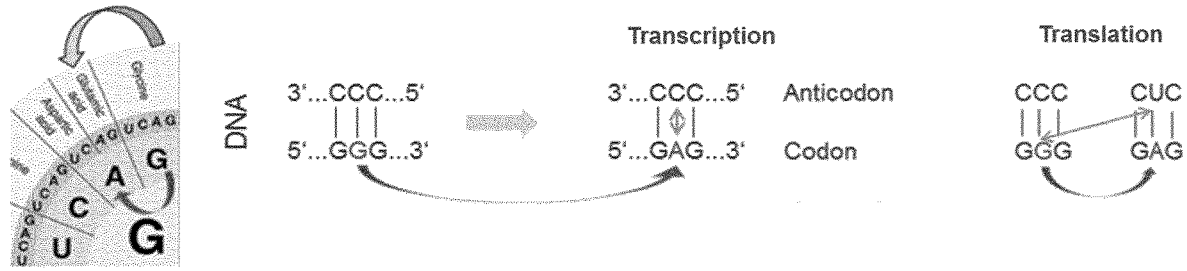
FIG. 2. (A) Scheme showing a G→A base difference in the genetic code resulting from a C*A mismatch due to non-Watson-Crick base pairing between the template strand of a DNA and an mRNA being transcribed, or a G*U mismatch between the mRNA codon and a tRNA anticodon, respectively, leading to a misincorporation of Glu in place of Gly in the translated polypeptide (Gly-Glu). (B) Scheme showing a U→C base difference in the genetic code resulting from an A*C mismatch due to non-Watson-Crick base pairing between the template strand of a DNA and an mRNA being transcribed, or a U*G mismatch between the mRNA codon and a tRNA anticodon, respectively, leading to a misincorporation, e.g., of Pro in place of Leu in the translated polypeptide (Leu→Pro). (C) Scheme showing a U→A base difference in the genetic code resulting from an A*A mismatch due to non-Watson-Crick base pairing between the template strand of a DNA and an mRNA being transcribed, or a U*U mismatch between the mRNA codon and a tRNA anticodon, respectively, leading to a misincorporation, e.g., of His in place of Leu in the translated polypeptide (Leu-His).
Figure 2B:
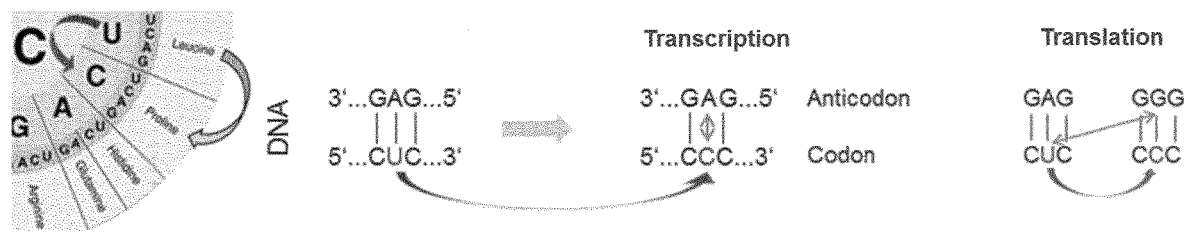
Figure 2C:
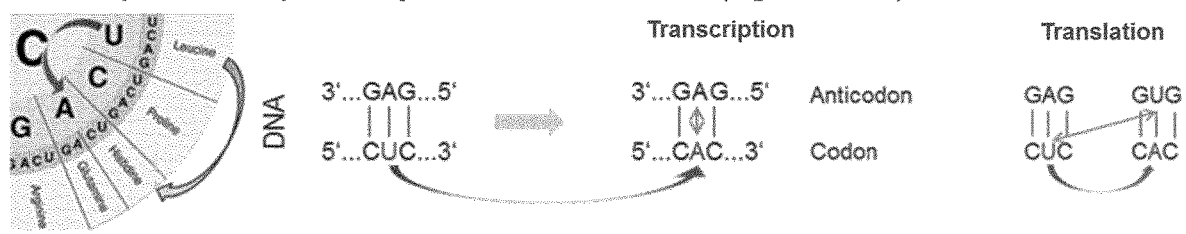

Sequence variant 1 comprises a Glu residue instead of Gly residue at amino acid position 4, as highlighted in Table 4. A Glu residue being misincoporated instead of Gly can be explained either by a C*A mismatch during transcription or a G*U mismatch during translation, as shown in FIG. 2A. Both mismatches lead to a base difference of G for A in the genetic code. According to the above disclosed Reverse-Engineering Matrix (Table 3) the codon at the respective position within the encoding polynucleotide can be identified to be either GGG or GGA, since the alternative codons GGC or GGU would have lead to another sequence variant comprising Asp at position 4 of the above exemplary peptide, as schematically depicted in FIG. 3.

Sequence variants 2 or 3 each comprise an Asp residue misincorporation instead of a Gly residue at amino acid position 5, or amino acid position 10, respectively, as highlighted in Table 4

Figure 3:
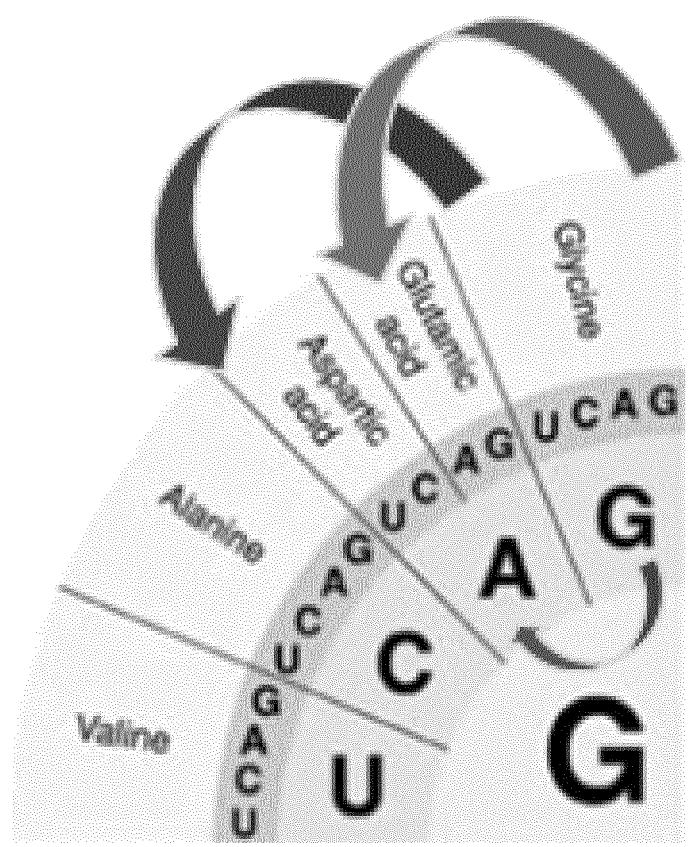
FIG. 3. Scheme of a G→A base difference at the level of the standard genetic code due to non-Watson-Crick base pairing. Depending on the codon, such base difference results in an amino acid residue misincorporation of either Gly→Glu, or Gly-Asp at the protein level. Thus, the presence of either one amino acid residue misincorporation is indicative of at least one codon being susceptible for amino acid misincorporation.

According to the scheme depicted in FIG. 3 the codon encoding the amino acid at these positions must be either GGC or GGU, since only these codons could have lead to a sequence variant comprising Asp at positions 5 or 10, respectively.

Figure 4:
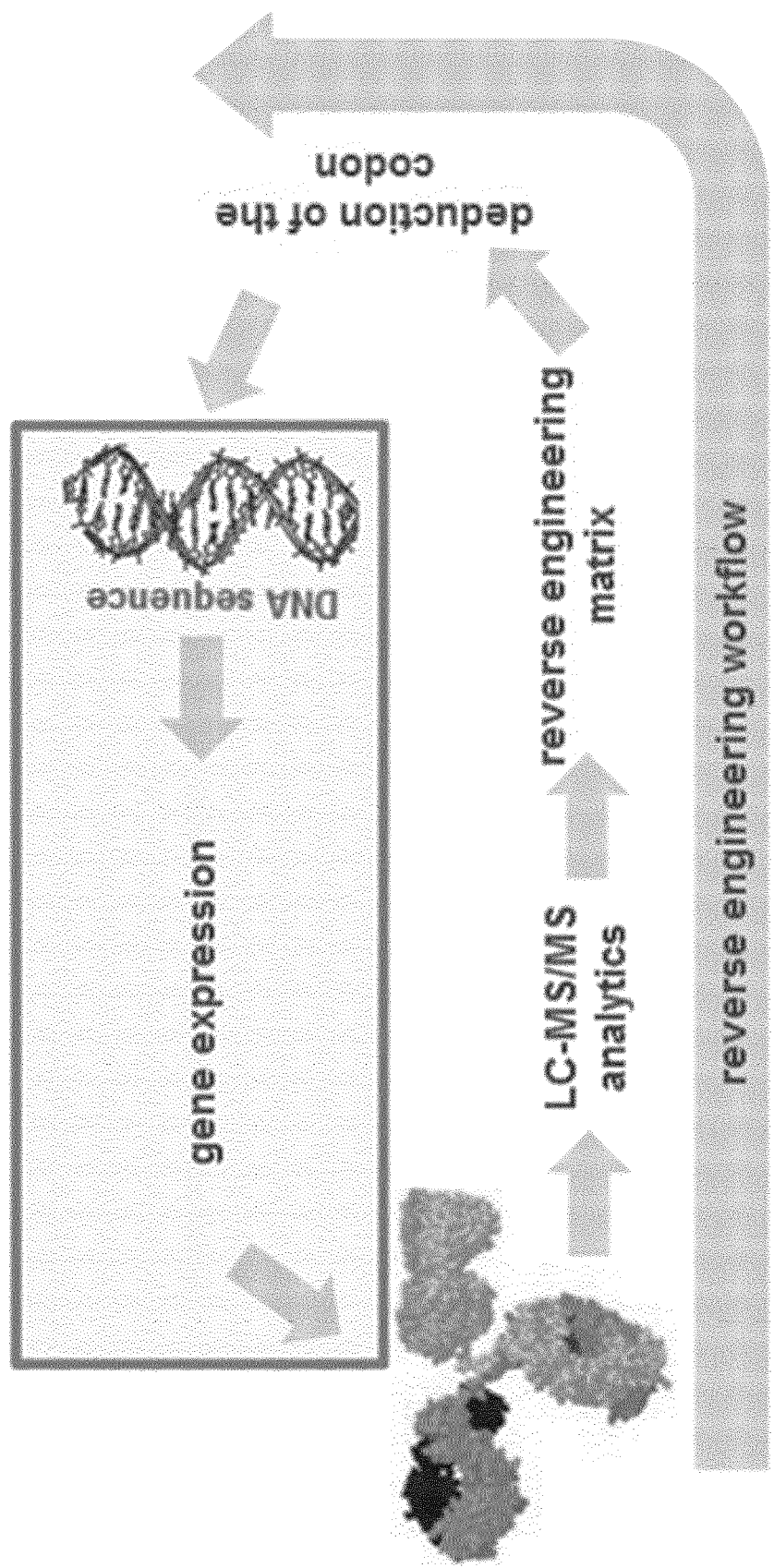
FIG. 4. Schematic work-flow of reverse engineering.

The workflow of optimizing the coding sequence of a polynucleotide by reverse engineering is schematically depicted in FIG. 4. The reverse-engineering matrix as disclosed in Table 3 is at the core of this workflow and provides the connection between any identified sequence variant and the respective at least one codon.

LC-MS/MS analysis used above is within the routine of a person skilled in the art. In short, the trypsin digest of a polypeptide sample is separated, e.g., by reversed-phase LC. Detection is performed on a state-of-the-art mass spectrometer, e.g., a Q Exactive™ Hybrid Quadrupole-Orbitrap Mass Spectrometer (ThermoFisher). Low level sequence variants are present at abundancies of 0.001% to 0.1% relative to the native peptide. Thus, the mass spectrometer being used must be of sufficient sensitivity. Data acquisition is followed by data evaluation using an appropriate MS analysis software package, as broadly available in the prior art, e.g., Xcalibur™ Software package (ThermoFisher).

Example 2—Reverse Engineering

The polypeptide obtainable by expression from the polynucleotide to be optimized by reverse-engineering is digested in silico, e.g., by trypsin. Amino acid residues Gly, Ser, Arg, Val, Ile, Leu and Met are replaced by their respective sequence variants in accordance with the reverse engineering matrix as disclosed in Table 3, and are tested for their presence in the acquired MS data, preferably using an extracted ion chromatogram (EIC). If a particular type of amino acid residue is present more than once within a peptide, its position must be determined using an MS/MS experiment, as exemplary shown in FIG. 5.

Figure 5:
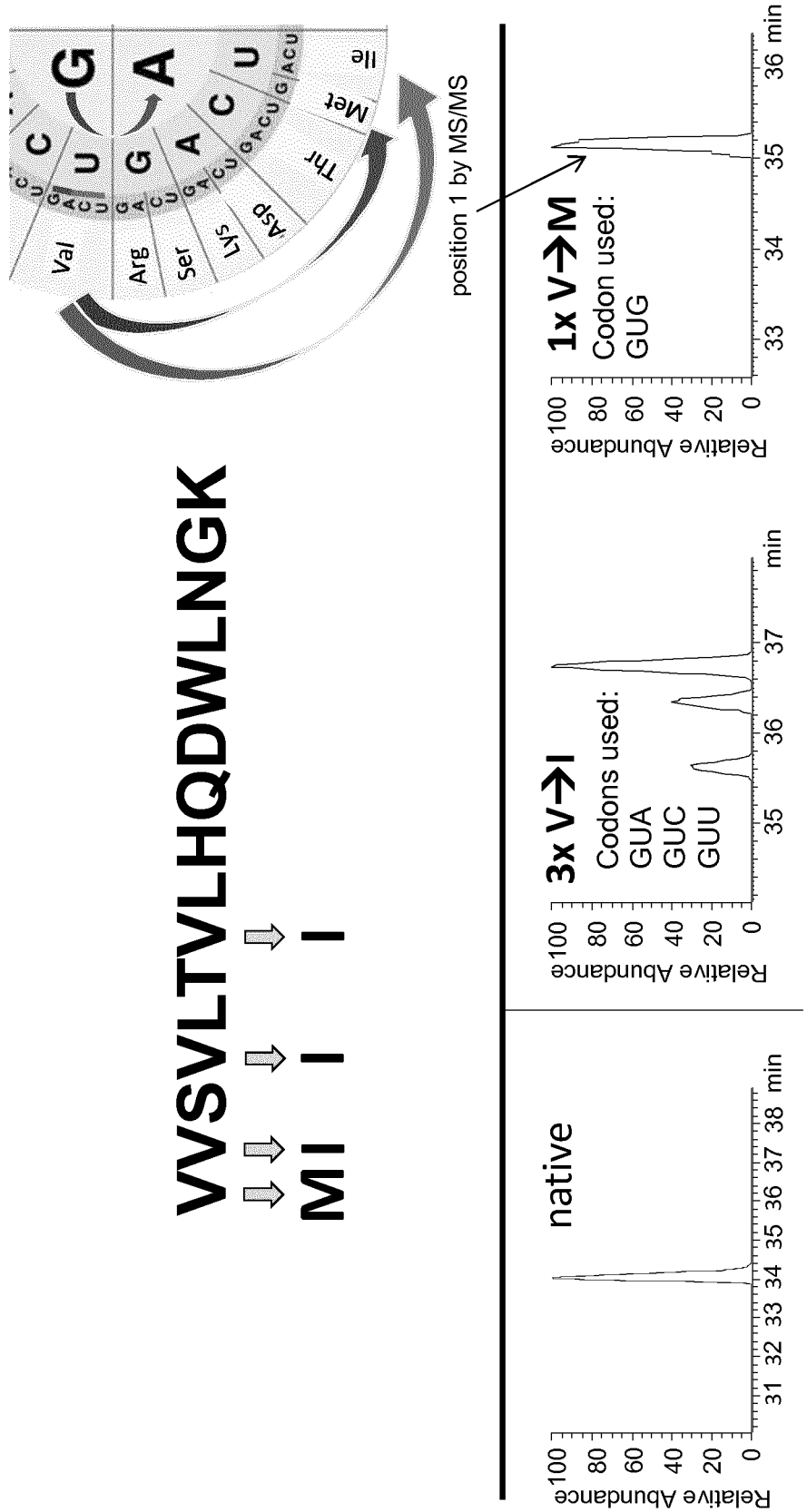
FIG. 5. Detection of low level sequence variants comprising the misincorporations Val→Met or Val→Ile.

The exemplary peptide VVSVLTVLHQDWLNGK (SEQ ID. No. 5) contains amino acid residues Gly, Ser and Val, which can be used for the method of the invention for reverse engineering at least one codon of the polynucleotide encoding the peptide. FIG. 5 shows the analysis of the amino acid residue misincorporations Val to Met (V→M) and Val to Ile (V→I). In accordance with the reverse-engineering matrix of Table 3, the codons encoding Val are susceptible for amino acid residue misincorporations within low level sequence variants, namely V→I, V→M, V→D, or V→K.

The theoretical masses of each possible peptide comprising said amino acid residue misincorporations is calculated and the EICs are extracted. As shown in FIG. 5, three peaks are found for the amino acid misincorporation V→I and one peak is found for the amino acid misincorporation V→M, summing up to the four Val residues comprised in the polypeptide. The peaks of each of the low level sequence variants is found in immediate chromatographic vicinity (±5 min) of the peak of the native peptide. To determine the position of the amino acid misincorporation(s), suitable MS/MS spectrograms are to be acquired. In the present example, the determination of the V→M position is sufficient, since it can be deduced from the reverse-engineering matrix of Table 3, that a. the first Val at position 1 is encoded by the codon GUG;
    b. the second, third and fourth Val at positions 2, 4 and 7 are either encoded by GUA, GUC or GUU (see FIG. 5) respectively.

In addition, the peptide can also be tested for the low level sequence variants V→D and V→K (due to a U*U mismatch), which allows for a narrowed determination of the respective codon encoding the second, third and fourth Val at positions 2, 4 and 7.

The at least one codon determined according to the above method can be used in optimizing the encoding polynucleotide sequence by (partial) reverse-engineering. Once at least one codon within the encoding polynucleotide sequence has been optimized according to the above method, the polynucleotide can be readily provided either by complete synthesis, or genetic engineering and molecular cloning techniques.

In this manner, it is possible to provide a polynucleotide encoding a polypeptide, e.g., a biosimilar exhibiting the same pattern of sequence variants as compared to an original biopharmaceutical polypeptide, of which the coding sequence is not known, or not fully known.

Example 3—Codon Optimization to Reduce the Immunogenic Potential (CORIP)

Gly can be encoded by GGA, GGG, GGC and GGU, or the DNA counterpart, respectively, see Table 2. According to Table 2 above, the following amino acid misincorporations can occur:

a. Gly→Asp or Gly→Ser (Codons: GGC or GGU); or
    b. Gly→Glu or Gly→Arg (Codon: GGG or GGA).

To decide which codon should be selected to encode glycine at the individual positions in order to decrease the immunogenic potential of the corresponding polypeptide, each Gly residue is individually substituted in silico by each of the aforementioned four potentially misincorporated amino acid residues. For example, in a given polypeptide sequence containing ten glycine residues, a total of 50 hypothetical protein sequences will be generated; 10 for the native protein and 10 each where one Gly residue in the sequence is substituted by Asp, Ser, Glu or Arg.

Next, the obtained protein sequences are subjected to an in silico prediction of T helper cell epitopes using computational tools as described in the literature (e.g. NetMHCII-pan, as described above). For each site it is then decided which codon will be used depending on the predicted MHC II affinity. In vitro or in vivo studies are optional to verify the in silico prediction (e.g. MHC II binding of synthesized peptides; T cell activation assay or MAPPS assay, as described above).

Figure 6:
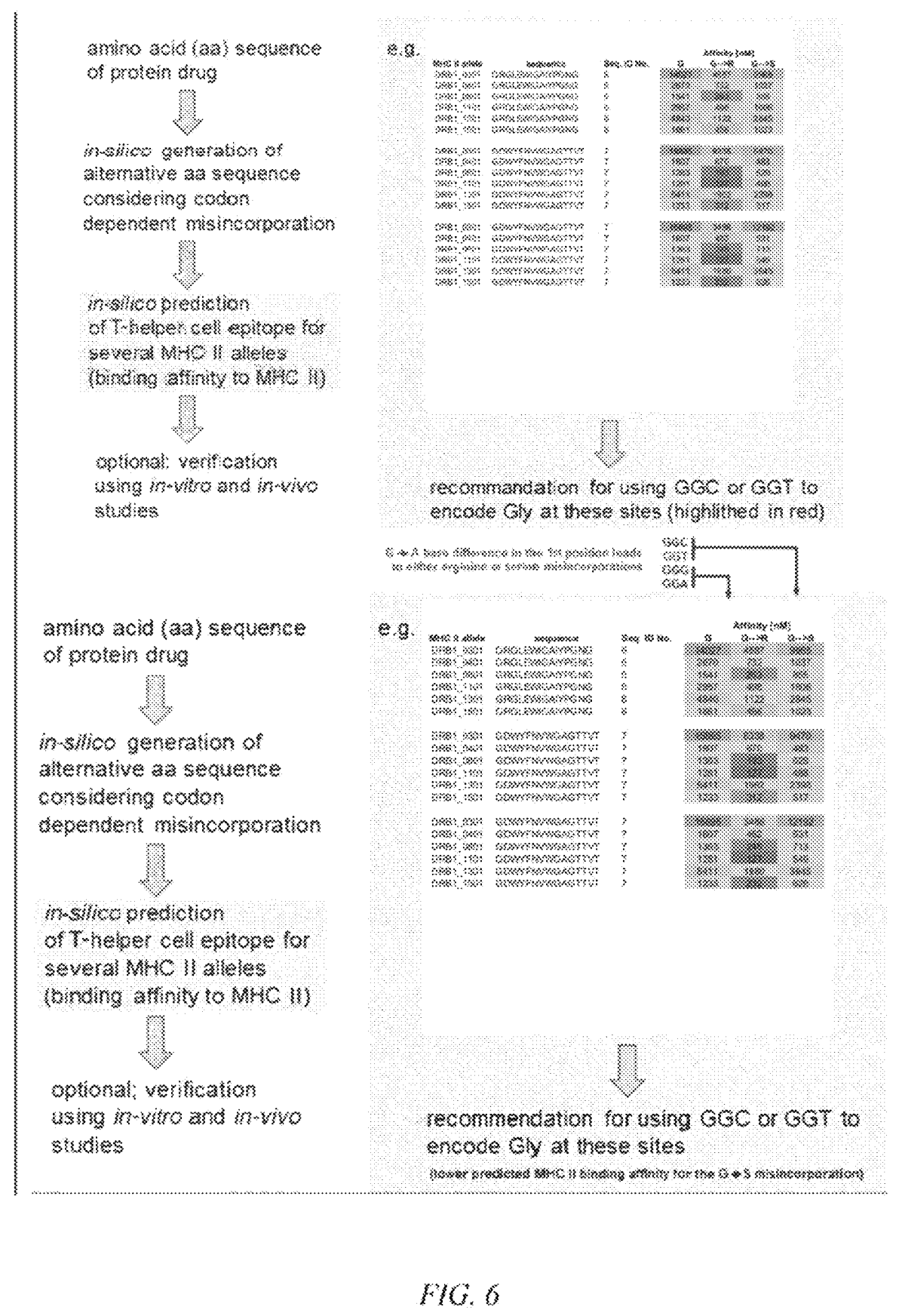

The scheme depicted in FIG. 6 further exemplifies this procedure: In this example, a polypeptide comprising the amino acid sequence GRGLEWIGAIYPGNG (SEQ ID. No. 6) is provided which comprises five Gly residues. FIG. 6 highlights three of the Gly residues which have been changed to Arg or Ser, respectively. In silico prediction of the immunogenic potential was performed using the NetMHCIIpan server for six representative MHC II alleles (Southwood et al., J Immunol 1998, 160(7):3363-73). The in silico prediction of immunogenic potential shows that the MHC II binding ($IC_{50}$ values) is negatively influenced by both substitutions but to a larger extent by the Gly→Arg misincorporation (resulting from a transcriptional and/or translation mismatch within a GGA or GGG codon). In the same exemplary manner, in silico predictions of the immunogenic potential were generated using the misincorporations Asp (resulting from a transcriptional and/or translation mismatch within a GGC or GGU codon) and Glu (resulting from a transcriptional and/or translation mismatch within a GGG or GGA codon).

In summary, the increased affinity towards the MHC II complex of the Gly→Arg misincorporation as compared to the Gly→Ser misincorporation potentially reflects a T helper cell epitope. Therefore it is recommendable to select the codons GGC or GGU to encode for Gly at the described positions.

Table 2 also shows that for a number of amino acid residues all available codons lead to the same misincorporation (e.g. all 2 codons for Y lead to a H or N misincorporation). In such a scenario, in silico prediction cannot be performed. However, if necessary, the gene of interest could be designed with both codons and subsequent in vitro or in vivo assays as mentioned above, could help to identify and select at least one codon which results in a reduction of the immunogenic potential of the polypeptide, e.g. a decrease in MHC II binding or a decrease in T cell activation.

The invention claimed is:

1. A method for optimizing the coding sequence of a polynucleotide that encodes a polypeptide, the method comprising
   (a) changing at least one codon within said coding sequence to an alternative codon, wherein said at least one codon is susceptible to amino acid residue misincorporation at a position within the encoded polypeptide that corresponds to said codon so as to change the degree or type of amino acid residue misincorporation; or
   (b) identification of at least one codon within said coding sequence which is susceptible to amino acid residue misincorporation at a position within the encoded polypeptide that corresponds to said codon and changing said codon to an alternative codon so as to change the degree or type of amino acid residue misincorporation
   wherein the polypeptide is recombinantly expressed from the polynucleotide coding sequence incorporating the alternative codon, by transcription and/or translation of the coding sequence in a host cell; and wherein said method comprises determining the degree or type of amino acid residue
   misincorporation found in:
      a) the polypeptide obtained by expression of said polynucleotide to be optimized; and/or
      b) a polypeptide obtainable by expression of a second polynucleotide which encodes the same polypeptide but differs in said at least one codon from the polynucleotide to be optimized;
      wherein determining the degree or type of amino acid residue misincorporation comprises the use of mass spectrometry (MS), and
   wherein a codon susceptible to amino acid residue misincorporation is a codon that, if altered by at least one base difference due to non-Watson-Crick base mismatches during transcription or translation, would encode another amino acid residue.

2. The method of claim 1, wherein said at least one codon is changed so as to match the degree or type of amino acid residue misincorporation found within a polypeptide obtainable by expression of a second polynucleotide which encodes the same polypeptide but differs in said at least one codon from the polynucleotide to be optimized.

3. The method of claim 1, wherein said method comprises determining the degree or type of amino acid residue misincorporation found in a polypeptide obtainable by expression of a second polynucleotide which encodes the same polypeptide but differs in said at least one codon from the polynucleotide to be optimized, and
   wherein said at least one codon is changed so as to match the degree or type of amino acid residue misincorporation found within said polypeptide obtainable by expression of said second polynucleotide which encodes the same polypeptide but differs in said at least one codon from the polynucleotide to be optimized.

4. The method of claim 1, wherein the amino acid residue misincorporation results in an increase in immunogenic potential of said polypeptide.

5. The method of claim 1, wherein the change of said at least one codon results in a decrease in immunogenic potential of said polypeptide.

6. The method of claim 4, wherein the immunogenic potential is determined in silico, in vitro or in vivo.

7. The method of claim 1, wherein the amino acid residue misincorporation is the result of at least one non-Watson-Crick base mismatch during transcription or translation.

8. The method of claim 7, wherein the at least one non-Watson-Crick base mismatch is selected from the group consisting of
   (a) a C*A mismatch between a DNA template strand and an mRNA being transcribed from said DNA template strand;
   (b) a G*U mismatch between the mRNA codon and an anticodon of an amino-acyl tRNA during translation;
   (c) an A*C mismatch between a DNA template strand and an mRNA being transcribed from said DNA template strand;
   (d) an U*G mismatch between the mRNA codon and an anticodon of an amino-acyl tRNA during translation;
   (e) an A*A mismatch between a DNA template strand and an mRNA being transcribed from said DNA template strand; or
   (f) an U*U mismatch between the mRNA codon and an anticodon of an amino-acyl tRNA during translation.

9. The method of claim 1, wherein the at least one codon encodes an amino acid residue selected from the group consisting of glycine, serine, arginine, valine, isoleucine, leucine and methionine.

10. The method of claim 1, wherein:
   (a) the at least one codon is GGC or GGU and aspartate is misincorporated in place of glycine;
   (b) the at least one codon is GGG or GGA and glutamate is misincorporated in place of glycine;
   (c) the at least one codon is GGG or GGA and arginine is misincorporated in place of glycine;
   (d) the at least one codon is GGC or GGU and serine is misincorporated in place of glycine;
   (e) the at least one codon is AGC or AGU and asparagine is misincorporated in place of serine;
   (f) the at least one codon is CGG or CGA and glutamine is misincorporated in place of arginine;
   (g) the at least one codon is CGU or CGC and histidine is misincorporated in place of arginine;
   (h) the at least one codon is AGG or AGA and lysine is misincorporated in place of arginine;
   (i) the at least one codon is GUA, GUU, or GUC and isoleucine is misincorporated in place of valine;
   (j) the at least one codon is GUG and methionine is misincorporated in place of valine;
   (k) the at least one codon is UUA or UUG and serine is misincorporated in place of leucine;
   (l) the at least one codon is UCU, UCC, UCA or UCG and proline is misincorporated in place of serine;

(m) the at least one codon is GUG or GUA and glutamate is misincorporated in place of valine;
(n) the at least one codon is GUC or GUU and aspartate is misincorporated in place of valine;
(o) the at least one codon is AUA and lysine is misincorporated in place of isoleucine;
(p) the at least one codon is AUC or AUU and asparagine is misincorporated in place of isoleucine;
(q) the at least one codon is AUG and lysine is misincorporated in place of methionine;
(r) the at least one codon is CUU or CUC and histidine is misincorporated in place of leucine;
(s) the at least one codon is CUA or CUG and glutamine is misincorporated in place of leucine;
(t) the at least one codon is UUA and isoleucine is misincorporated in place of leucine; or
(u) the at least one codon is UUG and methionine is misincorporated in place of leucine.

11. The method of claim 1, wherein the use of mass spectrometry comprises the use of LC-MS/MS, HPLC-MS/MS, nano-LC-MS/MS, or nanoHPCL-MS/MS.

12. The method of claim 1, wherein the polypeptide is a pharmaceutically active polypeptide.

13. A method for engineering a polynucleotide that encodes a polypeptide, comprising the following steps:
(a) optimizing the coding sequence according to the method of claim 1;
(b) substituting one or more nucleotide(s) of the polynucleotide to be engineered by the corresponding nucleotide(s) of the optimized coding sequence.

* * * * *